United States Patent [19]

Sugihara et al.

[11] Patent Number: 4,564,612

[45] Date of Patent: Jan. 14, 1986

[54] CONDENSED, SEVEN-MEMBERED RING COMPOUNDS AND THEIR USE

[75] Inventors: Hirosada Sugihara, Osaka; Kohei Nishikawa, Kyoto; Katsumi Ito, Osaka, all of Japan

[73] Assignee: Takeda Chemical Industries, Ltd., Osaka, Japan

[21] Appl. No.: 599,187

[22] Filed: Apr. 11, 1984

[30] Foreign Application Priority Data

| Apr. 22, 1983 | [JP] | Japan | PCT/JP83/00127 |
| Oct. 13, 1983 | [JP] | Japan | PCT/JP83/00342 |
| Mar. 22, 1984 | [JP] | Japan | PCT/JP84/00119 |

[51] Int. Cl.$^4$ .................. A61K 31/55; C07D 281/10
[52] U.S. Cl. .................. 514/211; 260/239.3 T; 260/239.3 B
[58] Field of Search .............. 260/239.3 B, 239.3 T; 424/244; 514/211

[56] References Cited

U.S. PATENT DOCUMENTS

| 3,341,519 | 9/1967 | Krapcho | 260/239.3 B |
| 4,477,464 | 10/1984 | Spade et al. | 260/239.3 B |

FOREIGN PATENT DOCUMENTS

| 51391 | 5/1982 | European Pat. Off. | |
| 57998 | 8/1982 | European Pat. Off. | |
| 68173 | 1/1983 | European Pat. Off. | 260/239.3 R |
| 58-29779 | 2/1983 | Japan | 260/239.3 B |
| 2103614 | 2/1983 | United Kingdom | 260/239.3 B |

OTHER PUBLICATIONS

Chemical Abstracts, vol. 94, p. 657, (1981), Registry No. 94: 156884t.
Central Patent Index, Basic Abstracts Journal, Section B: FARMDOC, 01015 E/01 B02 TANA 02.05.80 J56156-218, (Mar. 3, 1982).
Central Patent Index, Basic Abstracts Journal, Section B: FARMDOC, 82663 E/39 B02 NIPK 18.02.81 J57136-581, (Nov. 24, 1982).
Central Patent Index, Basic Abstracts Journal, Section B: FARMDOC, 01471J/47 B02 HAMA 13.04.81 J57169-474 (Jan. 26, 1983).

*Primary Examiner*—Robert T. Bond
*Attorney, Agent, or Firm*—Wegner & Bretschneider

[57] ABSTRACT

Novel condensed, seven-membered ring compounds of the formula:

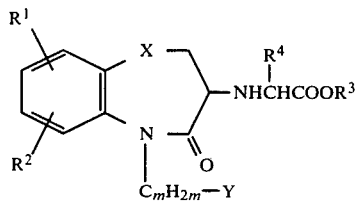

[wherein $R^1$ and $R^2$ each represent hydrogen, halogen, trifluoromethyl, lower alkyl or alkoxy, or both jointly form tri- or tetramethylene; $R^3$ is hydrogen, lower alkyl or aralkyl; $R^4$ is hydrogen or alkyl, aralkyl or cycloalkylalkyl which may be substituted; X is a group represented by the formula $S(O)_n$ (where n is an integer of 0 to 2); Y is a carboxyl group which may be esterified or amidated; m is 1 or 2] and salts thereof.

These compounds exhibit inhibitory activity on angiotensin converting enzyme and so forth, and are of value as an agent for diagnosis, prevention and treatment of hypertension.

9 Claims, No Drawings

CONDENSED, SEVEN-MEMBERED RING COMPOUNDS AND THEIR USE

TECHNICAL FIELD

The present invention relates to novel condensed, seven-membered ring compounds, which are useful as pharmaceuticals, and to a process for producing the same.

BACKGROUND ART

The present inventors, after extensive search for compounds which exhibit inhibitory activity on angiotensin converting enzyme and are useful as a therapeutic agent for circulatory diseases (e.g. hypertension, cardiopathy, cerebral apoplexy), succeeded in the production of novel condensed, seven-membered ring compounds having excellent action, and have completed the present invention.

DISCLOSURE OF THE INVENTION

The present invention provides novel compounds represented by the formula:

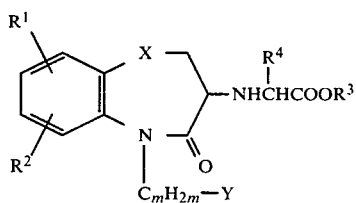

[wherein $R^1$ and $R^2$ are independently hydrogen, halogen, trifluoromethyl, lower alkyl or lower alkoxy, or both jointly form tri- or tetramethylene; $R^3$ is hydrogen, lower alkyl or aralkyl; $R^4$ is hydrogen or alkyl aralkyl or cycloalkylalkyl which may be substituted; X is a group represented by $S(O)_n$ wherein n is an integer of 0 to 2; Y is a carboxyl group which may be esterified or amidated; m means 1 or 2] and salts thereof.

Referring to the above formula (I), the halogen represented by $R^1$ and $R^2$ includes, for example, fluorine, chlorine, bromine, and iodine, and the lower alkoxy group represented by $R^1$ or $R^2$ includes alkoxy groups containing about 1–4 carbon atoms, such as methoxy, ethoxy, propoxy, isopropoxy, butoxy, isobutoxy, sec-butoxy, and tert-butoxy. Also, $R^1$ and $R^2$ both may combine with each other to form an alkylene bridge, whose examples include those such as trimethylene and tetramethylene.

The lower alkyl group represented by $R^1$, $R^2$ or $R^3$ includes alkyl groups containing about 1–4 carbon atoms, such as methyl, ethyl, propyl, isopropyl, butyl, isobutyl, sec-butyl and tert-butyl.

The alkyl group represented by $R^4$ includes straight chain or branched chain alkyl groups containing about 1–16 carbon atoms (e.g. methyl, ethyl, propyl, isopropyl, butyl, pentyl, isopentyl, hexyl, heptyl, octyl, nonyl, decyl, undecyl, dodecyl, tridecyl, tetradecyl, pentadecyl, hexadecyl), which may have as substituent moiety substituent groups such as hydroxyl, lower-($C_{1-4}$)-alkoxy (e.g. methoxy, ethoxy, propoxy, butoxy), mercapto, lower-($C_{1-4}$)-alkylthio (e.g. methylthio, ethylthio, propylthio, butylthio), amino, mono- or di-lower($C_{1-4}$)-alkylamino (e.g. methylamino, ethylamino, propylamino, isopropylamino, butylamino, isobutylamino, dimethylamino, methylethylamino, methylpropylamino, methylbutylamino, diethylamino, ethylpropylamino, ethylbutylamino, dipropylamino, propylbutylamino, dibutylamino), acylamino such as alkanoylamino containing not more than 5 carbon atoms (e.g. formamido, acetamido, propionamido, butyramido, valeramido, pyvalamido) and benzamido, $C_{3-8}$ cycloalkylamino (e.g. cyclopropylamino, cyclobutylamino, cyclopentylamino, cyclohexylamino, cycloheptylamino, cyclooctylamino). In case that $R^4$ is an substituted alkyl group as mentioned above, there is preferred 1 alkyl group contaning about 2 to 9 carbon atoms.

The aralkyl group represented by $R^3$ or $R^4$ includes phenyl-lower-($C_{1-4}$)-alkyl groups containing about 7 to 10 carbon atoms, such as benzyl, phenethyl, 3-phenylpropyl, α-methylbenzyl, α-ethylbenzyl, α-methylphenethyl, β-methylphenethyl and β-ethylphenethyl, wherein the phenyl and alkyl groups in said phenyl-lower-alkyl group may be substituted by 1 to 3 substituents sucy as halogen (e.g. fluorine, chlorine, bromine, iodine), $C_{1-4}$ alkyl group (e.g. methyl, ethyl, propyl, butyl group and the like), $C_{1-4}$ alkoxy group (e.g. methoxy, ethoxy, propoxy, isopropoxy, butoxy, methylenedioxy group and the like), amino, nitro or hydroxyl group. Examples of such substituted-phenyl-loweralkyl groups include 2-(4-chlorophenyl)ethyl, 2-(4-hydroxyphenyl)ethyl, 2-(4-methoxyphenyl)ethyl, 2-(3,4-dimethoxyphenyl)ethyl, 2-(3,4,5-trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl, 4-chlorobenzyl, α-aminophenethyl and β-aminophenethyl.

The cycloalkylalkyl group represented by $R^4$ includes $C_{3-8}$ cycloalkyl-lower-($C_{1-4}$)-alkyl groups containing about 4–12 carbon atoms, such as cyclopropylethyl, cyclobutylethyl, cyclopentylmethyl, cyclopentylethyl, cyclohexylmethyl, cyclohexylethyl, cyclohexylpropyl, cyclohexylbutyl, cycloheptylethyl and cyclooctylethyl; bicycloalkyl-lower-($C_{1-4}$)-alkyl groups, the bicycloalkyl moiety thereof being exemplified by for example norbornyl, bicyclo[2,2,2]octyl, bicyclo[3,3,1]nonyl or bicyclo[3,3,0]octyl; tricycloalkyl-lower ($C_{1-4}$)-alkyl groups, the tricycloalkyl moiety thereof being exemplified by for example adamantyl. Examples of the bicycloalkyl-lower-alkyl and tricycloalkyl-lower-alkyl groups include norbornylethyl, bicyclo[2,2,2]octylmethyl, bicyclo[3,3,1]nonylpropyl, bicyclo[3,3,0]octylbutyl, adamantylethyl, and the like. The cycloalkyl, bicycloalkyl, tricycloalkyl and lower alkyl groups in said $C_{3-8}$cycloalkyl-lower-alkyl, bicycloalkyl-lower-alkyl and tricycloalkyl-lower-alkyl groups may be substituted by 1 to 3 substituents such as halogen, $C_{1-4}$ alkyl, $C_{1-4}$ alkoxy, amino, nitro or hydroxy.

The group represented by X forms sulfide, sulfoxide or sulfone, depending upon its state of oxidation.

The esterified carboxyl group represented by Y includes lower-($C_{1-4}$)-alkoxycarbonyl groups, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, and phenyl-lower-($C_{1-4}$)-alkoxycarbonyl groups, such as benzyloxycarbonyl, α-phenethyloxycarbonyl, β-phenethyloxycarbonyl, phenylpropoxycarbonyl and phenylbutoxycarbonyl; the amidated carboxyl group includes carboxyl groups amidated with α-amino acids such as valine, leucine, isoleucine, threonine, Nα-lysine, methionine, phenylalanine and tryptophan, whereby the hydrogen atom of the carboxyl group in these α-amino acids may be substituted with lower-($C_{1-4}$)-alkyl (e.g. methyl, ethyl, propyl, butyl, tert-butyl, or phenyl-lower-($C_{1-4}$)-alkyl (e.g. benzyl, phenethyl, phenylpropyl, phenylbutyl).

The group represented by $C_mH_{2m}$ includes $CH_2$, $CH_2CH_2$ and $CH(CH_3)$.

The compounds of the present invention are specifically disclosed in the following:

3(R)-[1-Ethoxycarbonyl-3-phenylpropyl]amino-4-oxo-2,3,4,5-tetrahydro-1,5-benzothiazepine-5-acetic acid and its tert-butyl ester, 3(R)-[1-Ethoxycarbonyl-3-cyclohexylpropyl]amino-4-oxo 2,3,4,5-tetrahydro-1,5-benzothiazepine-5-acetic acid and its tert-butyl ester, 3(R)-[1-Ethoxycarbonyl-3-(p-tolyl)propyl]amino-4-oxo-2,3,4,5-tetrahydro-1,5-benzothiazepine-5-acetic acid and its tert-butyl ester, 3(R)-[1-Isobutoxycarbonyl-3-phenylpropyl]amino-4-oxo 2,3,4,5-tetrahydro-1,5-benzothiazepine-5-acetic acid and its tert-butyl ester, 7-Chloro-3(R)-[1-ethoxycarbonyl-3phenylpropyl]amino-4-oxo-2,3,4,5-tetrahydro-1,5-benzothiazepine-5-acetic acid and its tert-butyl ester, 3(R)-[1-Ethoxycarbonyl-3-phenylpropyl]amino-7-methoxy-4-oxo-2,3,4,5-tetrahydro-1,5-benzothiazepine-5-acetic acid and its tert-butyl ester, 3(R)-[1-Ethoxycarbonyl-3-phenylpropyl]amino-7-methyl-4-oxo-2,3,4,5-tetrahydro-1,5-benzothiazepine-5-acetic acid and its tert-butyl ester, 3(R)-[1-Ethoxycarbonyl-3-phenylpropyl]amino-4-oxo-7-trifluoromethyl-2,3,4,5-tetrahydro-1,5-benzothiazepine-5-acetic acid and its tert-butyl ester, 3(R)-[1-Ethoxycarbonyl-3-phenylpropyl]amino-4-oxo-2,3,4,5,8,9-hexahydro-7H-indeno[5,6-b][1,5]thiazepine-5-acetic acid and its tert-butyl ester, 3(R)-Ethoxycarbonylmethylamino-4-oxo-2,3,4,5-tetrahydro-1,5-benzothiazepine-5-acetic acid and its tert-butyl ester, 3(R)-[1-Benzyloxycarbonyl-3-phenylpropyl]-amino-4-oxo-2,3,4,5-tetrahydro-1,5-benzothiazepine-5-acetic acid and its tert-butyl ester, 3(R)-[1-Ethoxycarbonyl-4-methylpentyl]amino-4-oxo-2,3,4,5-tetrahydro-1,5-benzothiazepine-5-acetic acid and its tert-butyl ester, 3(R)-[1-Ethoxycarbonylnonyl]amino-4-oxo-2,3,4,5-tetrahydro-1,5-benzothiazepine-5-acetic acid and its tert-butyl ester, 3(R)-[1-Ethoxycarbonyl-3-phenylpropyl]amino-4-oxo-2,3,4,5-tetrahydro-1,5-benzothiazepin-5-yl-N-acetyl-L-phenylalanine and its tert-butyl ester, Benzyl 3(R)-[1-ethoxycarbonyl-3-phenylpropyl]amino-4-oxo-2,3,4,5-tetrahydro-1,5-benzothiazepine-5-acetate, 3(R)-[1-Ethoxycarbonyl-3-phenylpropyl]amino-4-oxo-2,3,4,5-tetrahydro-1,5-benzothiazepine-5-propionic acid, 3(R)-[1-Ethoxycarbonyl-3-phenylpropyl]amino-4-oxo-2,3,4,5-tetrahydro-1,5-benzothiazepine-5-acetic acid 1-oxide, 3(R)-[1-Ethoxycarbonyl-3-phenylpropyl]amino-4-oxo-2,3,4,5-tetrahydro-1,5-benzothiazepine-5-acetic acid 1,1-dioxide, 3(R)-[1-Ethoxycarbonyl-3-phenylpropyl]amino-4-oxo-2,3,4,5,7,8,9,10-octahydronaphtho[2,3-b][1,5]thiazepine-5-acetic acid and its tert-butyl ester, 3(R)-[3-Amino-1(S)-carboxypropyl]amino-4-oxo-2,3,4,5-tetrahydro-1,5-benzothiazepine-5-acetic acid, 3-(R)-[4-Amino-1(S)-carboxybutyl]amino-4-oxo-2,3,4,5-tetrahydro-1,5-benzothiazepine-5-acetic acid, 3(R)-[5-Amino-1(S)-carboxypentyl]amino-4-oxo-2,3,4,5-tetrahydro-1,5-benzothiazepine-5-acetic acid, 3(R)-[5-Amino-1(S)-ethoxycarbonylpentyl]amino-4-oxo-2,3,4,5-tetrahydro-1,5-benzothiazepine-5-acetic acid and its hydrochloride salt, 3(R)-[6-Amino-1(S)-carboxyhexyl]amino-4-oxo-2,3,4,5-tetrahydro-1,5-benzothiazepine-5-acetic acid, 3(R)-[6-Amino-1(S)-ethoxycarbonylhexyl]amino-4-oxo-2,3,4,5-tetrahydro-1,5-benzothiazepine-5-acetic acid, 3(R)-[7-Amino-1(S)-carboxyheptyl]amino-4-oxo-2,3,4,5-tetrahydro-1,5-benzothiazepine-5-acetic acid, 3(R)-[7-Amino-1(S)-ethoxycarbonylheptyl]amino-4-oxo-2,3,4,5-tetrahydro-1,5-benzothiazepine-5-acetic acid and its hydrochloride salt, 3(R)-[8-Amino-1(S)-carboxyoctyl]amino-4-oxo-2,3,4,5-tetrahydro-1,5-benzothiazepine-5-acetic acid, 3(R)-[8-Amino-1(S)-ethoxycarbonyloctyl]amino-4-oxo-2,3,4,5-tetrahydro-1,5-benzothiazepine-5-acetic acid, 3(R)-[9-Amino-1(S)-carboxynonyl]amino-4-oxo-2,3,4,5-tetrahydro-1,5-benzothiazepine-5-acetic acid, 3(R)-[9-Amino-1(S)-ethoxycarbonylnonyl]amino-4-oxo-2,3,4,5-tetrahydro-1,5,-benzothiazepine-5-acetic acid, 3(R)-[10-Amino-1(S)-carboxydecyl]amino-4-oxo-2,3,4,5-tetrahydro-1,5-benzothiazepine-5-acetic acid, 3(R)-[1(S)-Carboxy-5-(N-methylamino)pentyl]amino-4-oxo-2,3,4,5-tetrahydro-1,5-benzothiazepine-5-acetic acid, 3(R)-[1(S)-Carboxy-5-(N-ethylamino)pentyl]amino-4-oxo-2,3,4,5-tetrahydro-1,5-benzothiazepine-5-acetic acid, 3(R)-[1(S)-Carboxy-5-(N-isopropylamino)pentyl]amino-4-oxo-2,3,4,5-tetrahydro-1,5-benzothiazepine-5-acetic acid, 3(R)-[1(S)-Carboxy-5-(N,N-dimethylamino)pentyl]amino-4-oxo-2,3,4,5-tetrahydro-1,5-benzothiazepine-5-acetic acid, 3(R)-[1(S)-Carboxy-5-(N,N-diethylamino)pentyl]amino-4-oxo-2,3,4,5-tetrahydro-1,5-benzothiazepine-5-acetic acid, 3(R)-[1(S)-Carboxy-5-(N,N-dipropylamino)pentyl]amino-4-oxo-2,3,4,5-tetrahydro-1,5-benzothiazepine-5-acetic acid, 3(R)-[1(S)-Carboxy-5-(N,N-dibutylamino)pentyl]amino-4-oxo-2,3,4,5-tetrahydro-1,5-benzothiazepine-5-acetic acid, 3(R)-[5-Acetamido-1(S)-carboxypentyl]amino-4-oxo-2,3,4,5-tetrahydro-1,5-benzothiazepine-5-acetic acid, 3(R)-[5-Benzoylamino-1(S)-carboxypentyl]amino-4-oxo-2,3,4,5-tetrahydro-1,5-benzothiazepine-5-acetic acid, 3(R)-[1(S)-Carboxy-5-(N-cyclopentylamino)pentyl]amino-4-oxo-2,3,4,5-tetrahydro-1,5-benzothiazepine-5-acetic acid, 3(R)-[1(S)-Carboxy-5-(N-cyclohexylamino)pentyl]amino-4-oxo-2,3,4,5-tetrahydro-1,5-benzothiazepine-5-acetic acid and other chemical compounds.

Salts of the compounds (I) include pharmaceutically acceptable salts, such as salts with inorganic acid being exemplified by hydrochloride, hydrobromide, sulfate, nitrate, phosphate, etc., salts with organic acid being exemplified by acetate, tartarate, citrate, fumarate, maleate, toluenesulfonate, methanesulfonate, etc., metal salts being exemplified by sodium salts, potassium salts, calcium salts, aluminum salts, etc., and salts with bases being exemplified by triethylamine salts, guanidine salts, ammonium salts, hydrazine salts, quinine salts, cinchonine salts, etc.

The compound (I) of the present invention can be produced, for example, by subjecting a compound of the formula:

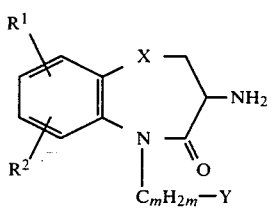  (II)

[wherein each of the symbols is as defined hereinbefore] and a compound of the formula:

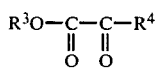  (III)

[wherein $R^3$ and $R^4$ are as defined hereinbefore] to a condensation reaction under reductive conditions.

The said reductive conditions include reaction conditions of catalystic reduction using metals, such as platinum, palladium, Raney nickel and rhodium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic reduction; reduction with reducing enzymes, and so forth. The above reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of −20° C. to +100° C. The reaction can be conducted at atmospheric pressure to achieve the desired object satisfactorily but may also be carried out under pressure or under reduced pressure according to the circumstances.

Also, the compound (I) of the present invention can be produced, for example, by subjecting a compound of the formula:

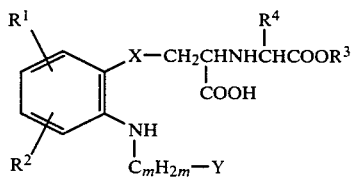  (IV)

[wherein each of the symbols is as defined hereinbefore] to a dehydrative ring-closure reaction. The said dehydrative ring-closure reaction can be carried out, for example, by means of an ordinary amide bond formation reaction in peptides synthesis. Thus, the reaction can be conducted by employing such a peptide forming reagent as dicyclohexylcarbodiimide, N,N′-carbonyldiimidazole, diphenylphosphorylazide and diethyl phosphorocyanidate solely or adding an ordinary acid (e.g. hydrochloric acid, sulfuric acid, nitric acid, hydrobromic acid) to allow protonation of the amino group of the compound (IV), and then condensing the protonated compound with phenols, such as 2,4,5-trichlorophenol, pentachlorophenol, pentafluorophenol, 2-nitrophenol or 4-nitrophenol, or N-hydroxy compounds, such as N-hydroxysuccinimide, 1-hydroxybenzotriazole and N-hydroxypiperidine, in the presence of such a catalyst as dicyclohexylcarbodiimide to convert to the active ester derivative, followed by cyclization. The cyclization reaction, in any cases of cylizing the compound (IV) as such or after converting to its activated ester, can be promoted by adding preferably organic bases, for example, quaternary ammonium salts or tertiary amines (e.g. triethylamine, N-methylpiperidine). The reaction temperature is normally −20° to +50° C., preferably in the neighborhood of room temperature, and the solvent which is normally employed includes, for example, dioxane, tetrahydrofuran, acetonitrile, pyridine, N,N-dimethylformamide, N,N-dimethylacetamide, dimethylsulfoxide, N-methylpyrrolidone, chloroform, methylene chloride, etc., which may be used alone or as a solvent mixture.

The compound of the present invention can also be produced, for example, by subjecting a compound of the formula:

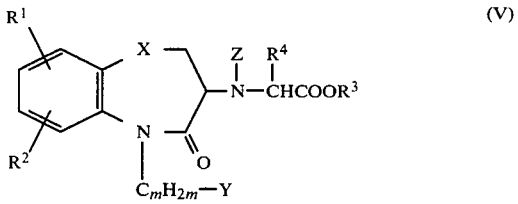  (V)

[wherein Z is a protective group removable by hydrolysis or catalytic reduction; other symbols are as defined hereinbefore] to a hydrolysis or catalytic reduction reaction. The protective group removable by hydrolysis as represented by Z in (V) includes all kinds of acyl groups and trityl group, and benzyloxycarbonyl, tert-butoxycarbonyl, trifluoroacetyl, trityl, etc., among others, are advantageous in the case of reactions under relatively mild reaction conditions. The protective group removable by catalytic reduction as represented by Z includes, for example, benzyl, diphenylmethyl, benzyloxycarbonyl, etc. The hydrolysis reaction in the said method is carried out in water or an organic solvent, such as methanol, ethanol, dioxane, pyridine, acetic acid, acetone and methylene chloride, or a solvent mixture thereof, and for the purpose of accelerating the reaction rate, it can be conducted as well by adding an acid (e.g. hydrochloride acid, hydrobromic acid, hydroiodic acid, hydrofluoric acid, sulfuric acid, methanesulfonic acid, p-toluenesulfonic acid, trifluoroacetic acid) or a base (e.g. sodium hydroxide, potassium hydroxide, potassium carbonate, sodium bicarbonate, sodium acetate, triethylamine). The above reaction is carried out normally within the range of about 31° to +150° C. The catalytic reduction reaction in the said method is conducted in water or an organic solvent, such as methanol, ethanol, dioxane and tetrahydrofuran, or a solvent mixture thereof in the presence of an appropriate catalyst, such as platinum and palladium-carbon. This reaction is carried out at atmospheric pressure or under pressure up to about 150 kg/cm² and at ordinary temperature or at a temperature up to +150° C., but the reaction generally proceeds satisfactorily at ordinary temperature and at atmospheric pressure.

The compound (I) of the present invention can be produced as well, for example, by subjecting the cyano group in a compound of the formula:

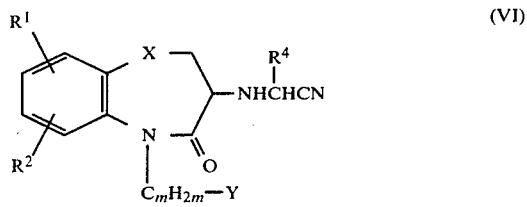

[wherein each of the symbols is as defined hereinbefore] to solvolysis.

The above solvolysis reaction is carried out in water or an organic solvent, such as methanol, ethanol, dioxane, pyridine, acetic acid, acetone and methylene chloride, or a solvent mixture thereof, and can also be conducted by adding an acid (e.g. hydrochloric acid, hydrobromic acid, hydroiodic acid, hydrofluoric acid, sulfuric acid, methanesulfonic acid, p-toluenesulfonic acid, trifluoroacetic acid) or a base (e.g. sodium hydroxide, potassium hydroxide, potassium carbonate, sodium bicarbonate, sodium acetate, triethylamine) for the purpose of accelerating the reaction rate. The reaction is normally carried out at a temperature within the range of about −20° to +150° C.

The compound (I) can also be produced by reacting the compound (II) with a compound of the formula:

[wherein R³ and R⁴ are as defined hereinbefore; W is halogen or a group represented by the formula $R^5SO_2$-O— (wherein R⁵ is lower alkyl, phenyl or p-tolyl)]. The reaction is allowed to proceed by maintaining both of the compounds in a suitable solvent within the temperature range of about −20° to +150° C. On this occasion, it is also possible for the purpose of accelerating the reaction rate to allow bases such as potassium carbonate, sodium hydroxide, sodium bicarbonate, pyridine and triethylamine to coexist in the reaction system.

The compound (I) of the present invention can also be produced, for example, by reacting a compound of the formula:

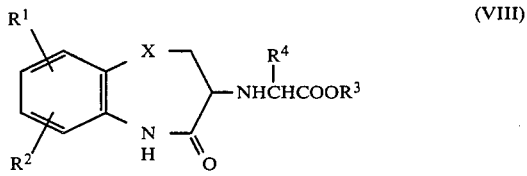

[wherein each of the symbols is as defined hereinbefore] with a compound of the formula:

[wherein W' is halogen or a group represented by the formula $R^{5'}SO_2$-O— (wherein R⁵ is lower alkyl, phenyl or p-tolyl); m and Y are as defined hereinbefore]. The reaction is allowed to proceed by maintaining both of the compounds in a suitable solvent within the temperature ranging about −20° to +150° C. On this occasion, the reaction can be conducted by allowing bases, such as potassium carbonate, sodium hydroxide and sodium hydride, to coexist in the reaction system.

In the case of the compound (I) wherein R³ is hydrogen and/or Y is carboxyl, the compound (I) can be produced as well by subjecting the ester compound wherein R³ is lower-($C_{1-4}$)-alkyl or/and Y is lower-($C_{1-4}$)-alkoxycarbonyl to a hydrolysis or elimination reaction, or by catalytic reduction of the benzyl ester compound wherein R³ is benzyl or/and Y is benzyloxycarbonyl.

In the case of the compound (I) wherein R³ is lower-($C_{1-4}$)-alkyl or/and Y is lower-($C_{1-4}$)-alkoxycarbonyl, further, such a compound can be produced as well by subjecting the compound wherein R³ is hydrogen or/and Y is carboxyl to an esterification reaction.

In the case of the compound (I) wherein Y is esterified or amidated carboxyl, such a compound can also be produced, for example, by condensing a compound of the formula:

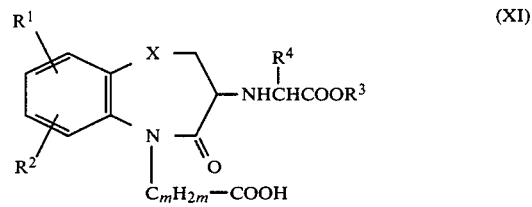

[wherein each of the symbols is as defined hereinbefore] with a compound of the formula:

[wherein R⁶ is a lower alcohol residue, phenyl-lower-alcohol residue or α-amino acid residue whose carboxyl group may be protected with lower alkyl or phenyl-lower-alkyl].

Furthermore, the compound of the formula:

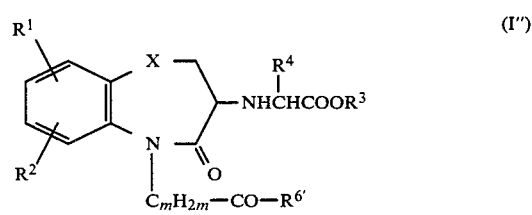

[wherein R⁶' is an α-amino acid residue; other symbols are as defined hereinbefore] can also be obtained by subjecting the compound obtained in the above condensation reaction as represented by the formula:

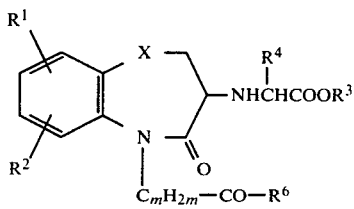

(I')

[wherein R[6] is α-amino acid residue whose carboxyl group is protected with lower alkyl or phenyl-lower alkyl and the other symbols is as defined hereinbefore], for example, to a hydrolysis reaction, elimination reaction or catalytic reduction.

In the case of the compound (I) wherein X is sulfoxide or sulfone, such a compound can be produced as well by oxidizing the corresponding sulfide compound. The said oxidation reaction is carried out, for example, by the action of an organic peracid (e.g. m-chloroperbenzoic acid, peracetic acid) or an inorganic oxidizing agent (e.g. hydrogen peroxide, periodic acid). The above reaction is normally conducted in the presence of water or an organic solvent (e.g. methanol, ethanol, dioxane, dichloromethane) within the temperature ranging from −20° to +100° C.

In case compounds having a group which may interfere with a reaction are used [e.g. reaction of the compound (II) with the compound (III) or (IV)], compounds wherein the said group is protected with a known protecting group [e.g. benzyloxycarbonyl, tert-butoxycarbonyl, chloroacetyl, phthalimide, succinimide] are subjected to the reaction, followed by per se known deprotection reaction to give the desired compound.

A compound of the formula:

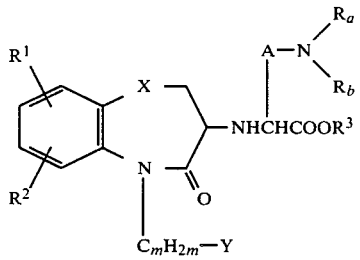

(Ia)

[wherein A is a straight or branched alkylene group containing about 1 to 16 carbon atoms, $R_a$ and $R_b$ are independently hydrogen, lower($C_{1-4}$)alkyl, acyl, cycloalkyl and the other symbols are as defined hereinbefore] can be produced for example by the following method.

The compound (II) is reacted with a compound of the formula:

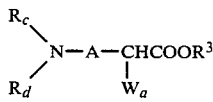

(VII')

[wherein $W_a$ is halogen or a group represented by the formula $R_eSO_2-O-$ (wherein $R_e$ is lower alkyl, phenyl or p-tolyl); one of $R_c$ and $R_d$ is hydrogen and the other is a protective group (e.g. benzoyl, acetyl) or both are cyclized with the adjacent nitrogen atom to form phthalimido or succinimido and the other symbols are as defined hereinbefore] to give a compound of the formula:

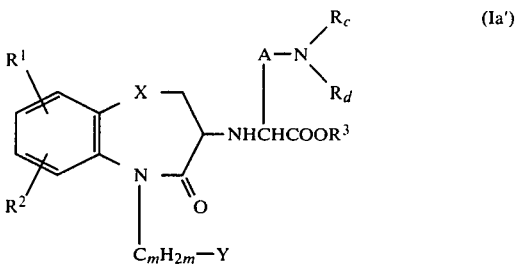

(Ia')

[wherein each of the symbols is as defined hereinbefore].

This compound (Ia') is subjected to deprotection reaction to give an amino compound (Ib) of the formula (Ia) wherein $R_a$ and $R_b$ are both hydrogen.

A compound of the formula (Ia) wherein $R_a$ and/or $R_b$ is lower alkyl or cycloalkyl, can be produced for example by reacting a corresponding aldehyde or ketone with the compound (Ib) under reductive conditions in water or an organic solvent (e.g. alcohol, ether, tetrahydrofuran, dimethylformamide, acetonitrile) or a mixture thereof, at a temperature ranging about −20° to +100° C.

The said reductive conditions include reaction conditions of catalytic reduction using metals, such as platinum, palladium, or mixtures thereof with arbitrary supports as a catalyst; reduction with metal hydride compounds, such as lithium aluminum hydride, lithium borohydride, lithium cyanoborohydride, sodium borohydride and sodium cyanoborohydride; reduction with metallic sodium, metallic magnesium, etc. and alcohols; reduction with metals such as iron or zinc and acids such as hydrochloric acid or acetic acid; electrolytic recution; reduction with reducing enzymes, and so forth.

A compound of the formula (Ia) wherein $R_a$ and/or $R_b$ is acyl, can be produced for example by reacting an activated organic acid derivative such as acid anhydride or acid halide with the compound (Ib) in water or an organic solvent (e.g. ethyl acetate, methylene chloride, ether, benzene, toluene, triethylamine, dimethylformamide) or a mixture thereof, at a temperature ranging from about −20° to +150° C. For accelerating the reaction rate, an organic base (e.g. triethylamine, picoline, pyridine) or an inorganic base (e.g. sodium bicarbonate) may be added.

The object compound (I) of the present invention thus obtained can be isolated from the reaction mixture by utilizing conventional separation and purification means, for example, means such as extraction, concentration, neutralization, filtration, recrystallization, column chromatography and thin layer chromatography.

Depending on the kind of the substituents represented by $R^4$, there may exist at least two stereoisomers of the compound (I). These individual isomers and mixture thereof, naturally, both fall within the scope of the present invention, and such isomers can be produced individually, if desired. For example, a single optical isomer of the compound (I) can be obtained by carrying out the above reaction using a single isomer each of the starting compounds (II), (IV), (V), (VI) and (VIII), and when the product is a mixture of two or more isomers, it can be separated into individual isomers by a usual separation technique, for example, separation means such as methods of forming salts with optically active acids (e.g. camphorsulfonic acid, tartaric acid, dibenzoyltartaric acid, etc.) or optically active bases (e.g. cinchonine, cinchonidine, quinine, quinidine, α-methylbenzylamine, dehydroabiethylamine, etc.), a variety of chromatographic techniques and fractional recrystallization.

The compound of the present invention, namely the condensed, seven-membered ring compounds represented by the formula (I) and a salt thereof, exhibit inhibitory activities on angiotensin converting enzyme, bradikinin decomposing enzyme (kininase), etc. in animals, in particular, mammals (e.g. human, dog, cat, rabbit, guinea pig, rat), and are useful, for example, as drugs for diagnosis, prevention or treatment of hypertension and hypertension-induced circulatory diseases (e.g. cardiopathy, cerebral apoplexy). The compound of the present invention is of low toxicity, well absorbed even on oral administration and highly stable and has long-lasting effect. Therefore, when it is used as the above-mentioned drugs, it can safely be administered orally or parenterally, per se or in admixture with suitable, pharmaceutically acceptable carriers, excipients or diluents in various pharmaceutical formulations such as powders, granules, tablets, capsules injectable solutions, etc. While the dosage level generally varies depending upon the conditions of the diseases to be treated as well as the administration route used, in the case of administration to human adult for the purpose of treatment of renal or essential hypertention, for example, the compound may be desirably administered orally at a single dose of about 0.02–20 mg/kg, preferably about 0.02–2 mg/kg, more preferably about 0.04–0.8 mg/kg, or intravenously at about 0.002–1 mg/kg, preferably about 0.002–0.2 mg/kg, more preferably about 0.02–0.2 mg/kg, about 1 to 5 times, preferably about 1 to 3 times, more preferably about once or twice per day according to the conditions.

The starting compounds (II), (IV), (V), (VI) and (VIII) of the present invention can be easily prepared, for example, by the methods as illustrated in the following reaction schema.

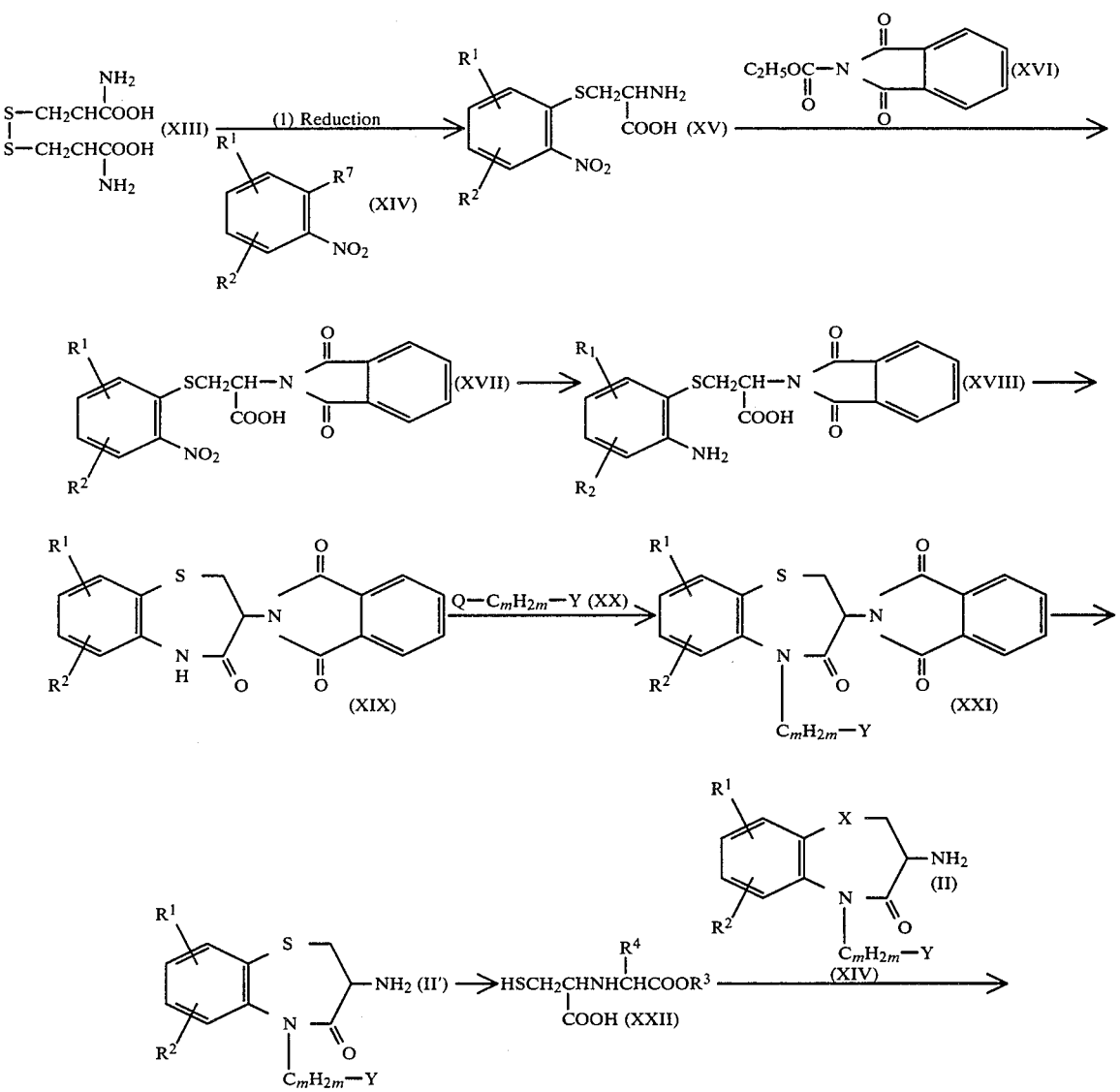

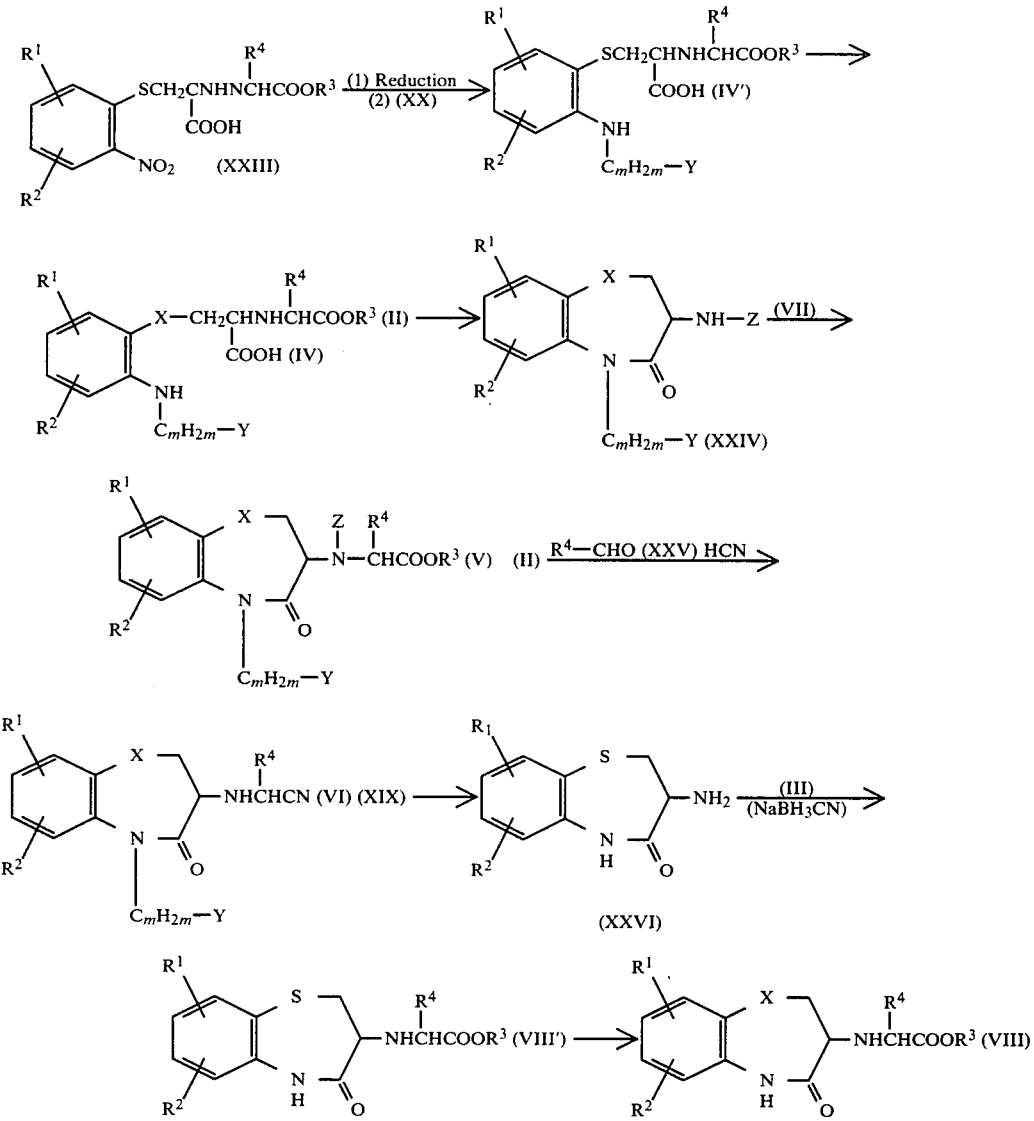

In the above reactions, $R^7$ is halogen or a diazonium group; Q is halogen or a group represented by the formula $R^8SO_2$—O— (wherein $R^8$ is lower alkyl, phenyl or p-tolyl); and other symbols are as defined hereinbefore.

The process for preparing the compound (II) as shown in the above reaction scheme is now illustrated in more detail. In accordance with the method of E. Boyland et al. (J. Chem. Soc., 1962, 606), the compound (XV) is derived from L-cystine (XIII) used as the starting compound, and subsequently, the amino group is protected with a suitable amino protective group (e.g. phthaloyl group) to give the compound (XVII). This reaction of the compound (XV) with N-carboethoxyphthalimide (XVI) is an aqueous solution proceeds readily in the presence of a base such as sodium carbonate, potassium carbonate and potassium bicarbonate normally at a temperature within the range of 0° to +100° C. The reaction of (XVII)→(XVIII) is involves reduction of the nitro group to the amino group, and conventionally known reduction techniques can be employed. Thus, the reaction technique includes catalytic reduction using as a catalyst for example palladium-carbon, palladium supported with barium sulfate, sulfided palladium, platinum, etc., reduction with such a metal as zinc, tin, stannous chloride or iron and acid or alkali, and so forth. The dehydrative ring-closure reaction of the resultant compound (XVIII) to the compound (XIX) can be advantageously carried out in the presence of a conventionally known dehydrative coupling agent. Such dehydrative coupling agent includes, for example, dicyclohexylcarbodiimide, carbonyldiimidazole, diethyl phosphorocyanidate, etc. As the solvent, use is made for example of dioxane, methylene chloride, acetonitrile, N,N-dimethylformamide, tetrahydrofuran, etc. and the reaction is normally conducted at a temperature in the range of −10° to +100° C. For the purpose of allowing the reaction to proceed advantageously, a base such as triethylamine or pyridine can also be added to the reaction solution as a catalyst. The preparation of the compound (XXI) through a condensation reaction between the compounds (XIX) and (XX) can be effected normally by condensation in a solvent such as N,N-dimethylformamide, dimethylsulfoxide and acetonitrile in the presence of such a base as sodium hydride, and potassium carbonate at a temperature in the range of about $-10°$ to $+100°$ C. Then, the reaction of (XXI)→(II') can be conducted by treating with hydrazine hydrate in a solvent such as methanol, ethanol or dioxane at a temperature in the range of about $-10°$ to $+100°$ C. to produce the compound (II').

The compound (II) where X is sulfoxide or sulfone can be produced by oxidizing the compound (II'). The said oxidation reaction is carried out for example by acting organic peracids (e.g. m-chloroperbenzoic acid, peracetic acid) or inorganic oxidizing agents (e.g. hydrogen peroxide, periodic acid). The above reaction is conducted normally in the presence of water or an organic solvent (e.g. methanol, ethanol, dioxane, dichloromethane), and performed normally at a temperature in the range of $-20°$ to $+100°$ C. Also, the said oxidation reaction can be applied to the compound (XV), (XVII), (XVIII), (XIX) or (XXI) to convert respective sulfide group to sulfoxide or sulfone, followed by subjecting to a series of reactions for the preparation of the compound (II) to yield the compound (II).

In the case of the compound (II) where X is sulfide, the compound (II') as the compound (II) can be subjected to the reaction for the production of the compound (I) to give the compound (I).

In the process for producing the compound (IV), the reaction of (XXII)→(XXIII) can be conducted in a manner similar to the reaction of (XIII)→(XV). The compound (IV') can be prepared by subjecting the compound (XXIII) to an ordinary reduction reaction of the nitro group to the amino group and subsequently to an alkylation reaction. In the case of the compound (IV) where X is sulfoxide or sulfone, such compound can be produced by subjecting to a reaction similar to the reaction of (II')→(II). In the case of the compound (IV) where X is sulfide, the compound (I) can be produced as well by subjecting the compound (IV') as the compound (IV) to the reaction. Also, the said oxidation reaction can be applied to the compound (XXIII) to convert the sulfide group to sulfoxide or sulfone, followed by subjecting to the reaction for the preparation of the compound (IV) to produce the compound (IV).

In the process for producing the compound (V), the compound (XXIV) can be produced by applying a per se known amino protecting reaction for amino acids to the compound (II). The reaction of (XXIV)→(V) is allowed to proceed by maintaining both of the compounds in an appropriate solvent within the temperature range of about $-20°$ to $+150°$ C. On this occasion, bases such as potassium carbonate, sodium hydroxide, sodium bicarbonate, pyridine and triethylamine can be made to coexist as a deacidifying agent in the reaction system for the purpose of accelerating the reaction rate.

In the process for producing the compound (VI), the compound (VI) can be obtained from the compounds (II) and (XXV) and hydrogen cyanide used as starting compounds according to the Strecker reaction which is per se known.

In the process for producing the compound (VIII), the reaction of (XIX)→(XXVI) can be promoted in a manner similar to the reaction of (XXI)→(II'). The compound (VIII') can be produced by condensing the compound (XXVI) with the compound (III) in the presence of a metal hydride such as sodium cyanoborohydride. In the case of the compound (VIII) where X is sulfoxide or sulfone, such compound can be produced by subjecting to a reaction similar to the reaction of (II')→(II). In the case of the compound (VIII) where X is sulfide, the compound (I) can also be produced by subjecting the compound (VIII') as the compound (VIII) to the reaction.

In the processes for producing the compound (I) and intermediates thereof, the compounds which are used in the reactions may be used in the form of salts, such as inorganic acid salts being exemplified by hydrochloride, hydrobromide, sulfate, nitrate, phosphate, etc., organic acid salts being exemplified by acetate, tartarate, citrate, fumarate, maleate, toluenesulfonate, methanesulfonate, etc., metal salts being exemplified by sodium salt, potassium salt, calcium salt, aluminum salt, etc., and salts with bases being exemplified by triethylamine salt, guanidine salt, ammonium salt, hydrazine salt, guinine salt, cinchonine salt, etc., so long as they do not interfere with such reactions.

Among the intermediates, the compound (Ia') has inhibitory activity on angiotensin converting enzyme and can be applied as a drug for diagnosis, prevention or treatment of hypertension in the same manner as the compound (I).

BEST MODE FOR CARRYING OUT THE INVENTION

REFERENCE EXAMPLE 1

To an aqueous solution (200 ml) of 1.4 g of sodium carbonate are added 2.9 g of S-(o-nitrophenyl)-L-cysteine and 3.5 g of N-ethoxycarbonylphthalimide. After being stirred at room temperature for 5 hours, the reaction mixture is filtered to remove the insoluble substance, and the filtrate is made weakly acid with concentrated hydrochloric acid. The deposited crystals are collected by filtration and recrystallized from 30 ml of ethanol to give 3.6 g of 3-(o-nitrophenyl)thio-2(R)-phthalimidopropionic acid as pale yellow needles.

m.p. 220°–222° C.

Elemental analysis, for $C_{17}H_{12}N_2O_6S$; Calcd.: C, 54.84; H, 3.25; N, 7.53; Found: C, 54.46; H, 3.26; N, 7.46; $[\alpha]_D^{24} = 79°$ (c=0.9, in methanol).

REFERENCE EXAMPLE 2

Catalytic reduction of 10 g of 3-(o-nitrophenyl)thio-2(R)-phthalimidopropionic acid in 300 ml of methanol is carried out at ordinary temperature and under atmospheric pressure using 5% palladium-carbon as catalyst. After absorption of the calculated amount of hydrogen, the catalyst is removed and the methanol is evaporated off under reduced pressure. The residue is crystallized from a mixture of ether and petroleum ether to give 8.4 g of 3-(o-aminophenyl)thio-2(R)-phthalimidopropionic acid as pale yellow crystals. To a stirred solution of 8.4 g of this product in 50 ml N,N-dimethylformamide is added dropwise 5.5 g of diethyl phosphorocyanidate at ice bath temperature. After the reaction mixture is stirred for 5 minutes, 2.28 g of triethylamine, is added dropwise at ice bath temperature. The resulting mixture is stirred for 30 minutes in an ice bath and for another 1 hour at room temperature, diluted with 200 ml of water and allowed to stand overnight. The deposited solid is collected by filtration and purified by silica gel column chromatography (dichloromethane:ethyl acetate=2:1) to give 5.4 g of 3(R)-phthalimido-2,3-dihydro-1,5(5H)-benzothiazepin-4-one as colorless prisms.

m.p. 202°–205° C.

Elemental analysis, for $C_{17}H_{12}N_2O_3S$; Calcd.: C, 62.95; H, 3.73; N, 8.64; Found: C, 63.15; H, 4.02; N, 8.49. $[\alpha]_D^{21} -164°$ (c=0.9, in methanol).

REFERENCE EXAMPLE 3

To a stirred mixture of 50 ml of N,N-dimethylformamide and 0.5 g of sodium hydride (60% in oil) is added 4 g of 3(R)-phthalimido-2,3-dihydro-1,5(5H)-benzothiazepin-4-one obtained in Reference Example 2 at ice bath temperature. After 5 minutes, 2 g of tert-butyl chloroacetate is added at ice bath temperature. The resulting mixture is stirred in an ice bath for b 15 minutes and diluted with ice water (200 ml). The deposited crystals are collected by filtration, dried and purified by silica gel column chromatography (hexane:ethyl acetate=3:1) to give 4 g of tert-butyl 4-oxo-3(R)-phthalimido-2,3,4,5-tetrahydro-1,5-benzothiazepine-5-acetate as colorless crystals. Recrystallization of a part of the crystals from ethyl ether yields colorless prisms, m.p. 181°-184° C.

Elemental analysis, for $C_{23}H_{22}N_2O_5S$; Calcd.: C, 63.01; H, 5.06; N, 6.39; Found: C, 62.95; H, 5.10; N, 6.34. $[\alpha]_D^{21} -156°$ (c=0.9, in chloroform)

REFERENCE EXAMPLE 4

A mixture of 100 ml of ethanol, 4 g of tert-butyl 4-oxo-3(R)-phthalimido-2,3,4,5-tetrahydro-1,5-benzothiazepine-5-acetate obtained in Reference Example 3 and 1.4 g of hydrazine hydrate is refluxed for 1 hour with stirring. The reaction mixture is concentrated under reduced pressure, and 300 ml of ethyl acetate and 100 ml of water are added to the residue, followed by shaking thoroughly. The ethyl acetate layer is washed successively with aqueous dilute sodium hydroxide and water, dried over anhydrous magnesium sulfate and concentrated under reduced pressure. The oily residue is crystallized from a mixture of ether and petroleum ether to give 2 g of tert-butyl 3(R)-amino-4-oxo-2,3,4,5-tetrahydro-1,5-benzothiazepine-5-acetate as colorless prisms, m.p. 86°-89° C.

Elemental analysis, for $C_{15}H_2N_{20}O_3S$; Calcd.: C, 58.42; H, 6.54; N, 9.08; Found: C, 58.73; H, 6.48; N, 9.13. $[\alpha]_D^{20} -238°$ C. (c=1, in methanol).

REFERENCE EXAMPLE 5

In 100 ml of ethanol is dissolved 4.5 g of sodium, and 30 g of ethyl 3-cyclohexylpropionate and 29 g of diethyl oxalate are added to the solution, followed by heating about 70° C. for 30 minutes. The low-boiling substance is removed by evaporation under reduced pressure at 70° C. for 30 minutes. After cooling, 500 ml of water, 200 ml of ether and 100 ml of petroleum ether are added to the brown viscous residue, and the mixture is thoroughly shaken. The aqueous layer is separated, acidified slightly with sulfuric acid and extracted with 200 ml of ethyl acetate. The extract is dried over anhydrous magnesium sulfate and concentrated under reduced pressure. One hundred and ten ml of 10% aqueous dimethylsulfoxide and 10 g of sodium chloride are added to the oily residue, and the mixture is stirred at 140° C. for 2.5 hours. After the reaction mixture is cooled, 1 l of water is added, followed by extraction with 500 ml of ethyl acetate. The extract is washed with water, dried over anhydrous magnesium sulfate and concentrated under reduced pressure. The brown oily residue is distilled under reduced pressure to give 18 g of ethyl 4-cyclohexyl-2-oxo-butyrate as a pale yellow liquid.

Boiling point: 105°-110° C. (1.5 mmHg).

REFERENCE EXAMPLES 6-10

By carrying out the reaction using substituted o-nitroaniline derivatives as a starting material similarly to the case of the non-substituent compound (R=H), the compounds as shown in Table 1 are obtained.

TABLE 1

| Ref. Ex. No. | R | Config. *1 | m.p. (°C.) | $[\alpha]_D$ (in 1 N HCl) |
|---|---|---|---|---|
| 6 | 4-CH₃ | R | 156-158 | +44° |
| 7 | 4-OCH₃ | R | 166-168 | +24° |
| 8 | 4,5-(CH₂)₃— | R | 157-158 | +33° |
| 9 | 4-Cl | R | 169-171 | +46° |
| 10 | 4-CF₃ | R | 181-183 | +53° |

REFERENCE EXAMPLES 11-14

The reaction of S-(2-nitrophenyl)-L-cysteine derivatives obtained in Reference Examples 6-9 with N-ethoxycarbonylphthalimide in a manner similar to that described in Reference Example 1, gives the compounds as shown in Table 2.

TABLE 2

| Ref. Ex. No. | R | Config. *1 | m.p. (°C.) | $[\alpha]_D$ (in methanol) |
|---|---|---|---|---|
| 11 | 4-CH₃ | R | used in the following reaction without purification | |
| 12 | 4-OCH₃ | R | 157-159 | -120° |
| 13 | 4,5-(CH₂)₃— | R | 219-222 | -149° |
| 14 | 4-Cl | R | 183-185 | -116° |

REFERENCE EXAMPLES 15-18

The phthalimide derivatives obtained in Reference Examples 11-14 are allowed to react in a manner similar to that described in Reference Example 2 to give the compounds as shown in Table 3.

TABLE 3

| Ref. Ex. No. | R | Config. *1 | m.p. (°C.) | $[\alpha]_D$ |
|---|---|---|---|---|
| 15 | 7-CH₃ | R | 222-225 | -180° (in methanol) |

TABLE 3-continued

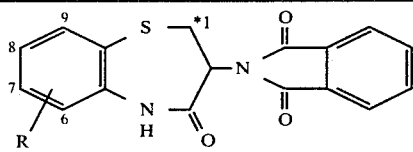

| Ref. Ex. No. | R | Config. *1 | m.p. (°C.) | $[\alpha]_D$ |
|---|---|---|---|---|
| 16 | 7-OCH$_3$ | R | 255-258 | -34° (in chloroform) |
| 17 | 7,8-(CH$_2$)$_3$— | R | 240-243 | -136° (in methanol) |
| 18 | 7-Cl | R | 256-258 | -169° (in methanol) |

REFERENCE EXAMPLES 19-22

The phthalimidobenzothiazepine derivatives obtained in Reference Examples 15-18 are allowed to react in a manner similar to that described in Reference Example 3 to give the compounds as shown in Table 4.

TABLE 4

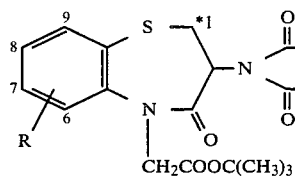

| Ref. Ex. No. | R | config. *1 | m.p. (°C.) | $[\alpha]_D$ (in methanol) |
|---|---|---|---|---|
| 19 | 7-CH$_3$ | R | 140-143 | -151° |
| 20 | 7-OCH$_3$ | R | 155-157 | -139° |
| 21 | 7,8-(CH$_2$)$_3$— | R | 195-198 | -114° |
| 22 | 7-Cl | R | 182-184 | -148° |

REFERENCE EXAMPLES 23-26

The tert-butyl phthalimidobenzothiazepine-acetate derivatives are allowed to react in a manner similar to that described in Reference Example 4, to give the compounds as shown in Table 5.

TABLE 5

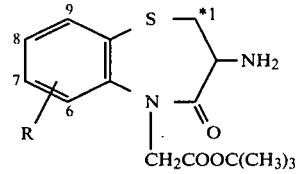

| Ref. Ex. No. | R | Config. *1 | m.p. (°C.) | $[\alpha]_D$ (in methanol) |
|---|---|---|---|---|
| 23 | 7-CH$_3$ | R | 159-160 (oxalate) | -146° |
| 24 | 7-OCH$_3$ | R | 175-178 (hydrochloride) | -147° |
| 25 | 7,8-(CH$_2$)$_3$— | R | used in the following reaction without purification | |
| 26 | 7-Cl | R | 158-160 (oxalate) | -102° |

REFERENCE EXAMPLES 27-30

By carrying out the reaction using the carboxylic acid ethyl ester as shown in Table 6 as a starting compound similarly to case of Reference Example 5, the corresponding α-keto ester derivative is obtained.

TABLE 6

| Ref. Ex. No. | Starting compound | Keto-ester compound obtained |
|---|---|---|
| 27 | CH$_3$(CH$_2$)$_7$COOC$_2$H$_5$ | CH$_3$(CH$_2$)$_7$COCOOC$_2$H$_5$ |
| 28 | (C$_6$H$_5$)$_2$CH—CH$_2$COOC$_2$H$_5$ | (C$_6$H$_5$)$_2$CHCH$_2$COCOOC$_2$H$_5$ |
| 29 | (CH$_3$)$_2$CH—CH$_2$CH$_2$COOC$_2$H$_5$ | (CH$_3$)$_2$CHCH$_2$CH$_2$COCOOC$_2$H$_5$ |
| 30 | 4-CH$_3$-C$_6$H$_{10}$-CH$_2$CH$_2$COOC$_2$H$_5$ | 4-CH$_3$-C$_6$H$_{10}$-CH$_2$CH$_2$COCOOC$_2$H$_5$ |

REFERENCE EXAMPLE 31

A mixture of 67 ml of 2.5N aqueous sodium hydroxide and 5.3 g of S-(2-nitro-4-trifluoromethylphenyl)-L-cysteine obtained in Reference Example 10 is stirred at room temperature for 30 minutes. Two point seven ml of benzyloxycarbonyl chloride and 19 ml of 1N aqueous sodium hydroxide are simultaneously added dropwise to the mixture at ice bath temperature over a period of 30 minutes. The resulting mixture is stirred at room temperature for further 2.5 hours and extracted with ethyl ether. The aqueous layer is acidified slightly with 1N hydrochloric acid and extracted with ethyl acetate. The extract is dried over anhydrous magnesium sulfate and concentrated under reduced pressure. The residue is crystallized from ethyl ether to yield 5.5 g of S-(2-nitro-4-trifluoromethylphenyl)-N-benzyloxycarbonyl-L-cysteine as pale yellow crystals, m.p. 150°–153° C.

$[\alpha]_D+20°$ (in methanol).

Elemental analysis, for $C_{18}H_{15}F_3N_2O_6S$; Calcd.: C, 48.65; H, 3.40; N, 6.30; Found: C, 48.68; H, 3.41; N, 6.27.

REFERENCE EXAMPLE 32

To a mixture of 50 ml of acetic acid and 50 ml of water are added 4.3 g of S-(2-nitro-4-trifluoromethylphenyl)-N-benzyloxycarbonyl-L-cysteine obtained in Reference Example 31 and 4 g of powdered zinc, and the mixture is stirred at room temperature for 50 minutes. One hundred and fifty ml of water and 150 ml of ethyl acetate are added, and the insoluble substance is filtered off. The aqueous layer is extracted twice with 100 ml of ethyl acetate. The ethyl acetate layers are combined, washed with water, dried over anhydrous magnesium sulfate and concentrated under reduced pressure. The residue is dissolved in 50 ml of ethyl ether, and 5 ml of hydrogen chloride-ethyl acetate solution (5N) is added to the solution to deposit 3.4 g of S-(2-amino-4-trifluoromethylphenyl)-N-benzyloxycarbonyl-L-cysteine hydrochloride as pale yellow powder. The product is dissolved in 30 ml of N,N-dimethylformamide, and a solution of 0.78 g of triethylamine in 5 ml of N,N-dimethylformamide is added dropwise to the stirred solution at ice bath temperature over a period of 10 minutes. After addition of a solution of 1.83 g of diethyl phosphorocyanidate in 5 ml of N,N-dimethylformamide over a period of 5 minutes, a solution of 0.78 g of triethylamine in 5 ml of N,N-dimethylformamide is added. The reaction mixture is stirred for 30 minutes in an ice bath and for further 2.5 hours at room temperature, diluted with 200 ml of water and extracted with ethyl acetate. The extract is dried over anhydrous magnesium sulfate and concentrated under reduced pressure. The oily residue is purified by silica gel column chromatography (hexane:ethyl acetate=4:1 to 2:1) to give 1.3 g of 3(R)-benzyloxycarbonylamino-7-trifluoromethyl-2,3-dihydro-1,5(5H)-benzothiazepin-4-one as colorless crystals, m.p. 120°–123° C.

$[\alpha]_D-161°$ (in methanol).

Elemental analysis, for $C_{18}H_{15}F_3N_2O_3S$; Calcd.: C, 54.54; H, 3.81; N, 7.07; Found: C, 54.79; H, 3.90; N, 7.09.

REFERENCE EXAMPLE 33

A mixture of 20 ml of N,N-dimethylformamide, 1.1 g of 3(R)-benzyloxycarbonylamino-7-trifluoromethyl-2,3-dihydro-1,5(5H)-benzothiazepin-4-one obtained in Reference Example 32, 0.46 g of tert-butyl chloroacetate, 0.42 g of potassium carbonate and 0.1 g of potassium iodide is stirred at room temperature for 4.5 hours. After 100 ml of water is added, the mixture is extracted with 100 ml of ethyl acetate. The extract is washed successively with 0.1N hydrochloric acid, aqueous sodium bicarbonate and water, dried over anhydrous magnesium sulfate and concentrated under reduced pressure to give 1.4 g of tert-butyl 3(R)-benzyloxycarbonylamino-4-oxo-7-trifluoromethyl-2,3,4,5-tetrahydro-1,5-benzothiazepine-5-acetate as a colorless viscous substance.

IR $\nu_{max}^{nujol}$ cm$^{-1}$: 1680 (amide); 1710 (urethane), 1740 (ester).

*IR: Infrared absorption spectrum: The same shall apply hereinafter.

REFERENCE EXAMPLE 34

To a solution of 1.4 g of tert-butyl 3(R)-benzyloxycarbonylamino-4-oxo-2,3,4,5-tetrahydro-1,5-benzothiazepine-5-acetate obtained in Reference Example 33 in 5 ml of acetic acid is added 10 ml of 30% hydrogen bromide-acetic acid solution. The mixture is allowed to stand at room temperature for 4 hours, and diluted with 100 ml of petroleum ether, followed by agitating thoroughly. The supernatant layer is removed by decantation. After another treatment of decantation, the precipiate is dissolved in a mixture of ethyl acetate and benzene and the solution is evaporated to dryness under reduced pressure. The residue is crystallized from petroleum ether to give 0.75 g of 3(R)-amino-4-oxo-7-trifluoromethyl-2,3,4,5-tetrahydro-1,5-benzothiazepine-5-acetic acid hydrobromide as crystals, m.p. 176°–180° C.

Elemental analysis, for $C_{12}H_{11}F_3N_2O_3S.HBr.H_2O$; Calcd.: C, 34.38; H, 3.37; N, 6.68; Found: C, 34.40; H, 3.60; N, 6.66.

REFERENCE EXAMPLE 35

A mixture of 20 ml of ethanol, 2 g of tert-butyl 3(R)-amino-4-oxo-2,3,4,5-tetrahydro-1,5-benzothiazepine-5-acetate obtained in Reference Example 4, 1.6 g of benzyl bromide and 1 g of triethylamine is allowed to stand at room temperature for 3 days. After 100 ml of water and 200 ml of ethyl acetate are added to the mixture, extraction is conducted. The extract is dried over anhydrous magnesium sulfate and concentrated under reduced pressure. The residue is purified by silica gel column chromatography (hexane:ethyl acetate=3:1) to yield 2 g of tert-butyl 3(R)-benzylamino-4-oxo-2,3,4,5-tetrahydro-1,5-benzothiazepine-5-acetate as a colorless oil. One point seven g of thus obtained product is dissolved in 30 ml of N,N-dimethylformamide, and potassium carbonate (1.7 g) and ethyl bromoacetate (1 ml) are added to the solution. The resulting mixture is heated at 80° C. for 2 hours. After further addition of 4 ml of ethyl bromoacetate and 3 g of potassium carbonate, the mixture is heated at 100° C. for another 8 hours. The reaction mixture is diluted with 300 ml of water and extracted with 400 ml of ethyl acetate. The extract is dried over anhydrous magnesium sulfate and concentrated under reduced pressure. The oily residue is purified by silica gel column chromatography (hexane:ethyl acetate=5:1) to give 1.6 g of tert-butyl 3(R)-(N-benzyl-N-ethoxycarbonylmethylamino)-4-oxo-2,3,4,5-tetrahydro-1,5-benzothiazepine-5-acetate as a colorless oil. The solution of 1 g of this product in 15 ml of hydrogen chloride-ethyl acetate solution (5N) is allowed to stand at room temperature for 4 hours, and diluted with 200 ml of petroleum ether to deposit 0.8 g of 3(R)-(N-benzyl-N-ethoxycarbonylmethylamino)-4-oxo-2,3,4,5-tetrahydro-1,5-benzothiazepine-5-acetic acid hydrochloride as colorless powder.

Elemental analysis, for $C_{22}H_{24}N_2O_5S.HCl$; Calcd.: C, 56.83; H, 5.42; N, 6.03; Found: C, 56.61; H, 5.59; N, 6.07.

$[\alpha]_D-164°$ (in methanol).

Mass spectrum (m/e): 428 (M+).

REFERENCE EXAMPLE 36

To a solution of tert-butyl 3(R)-amino-4-oxo-2,3,4,5-tetrahydro-1,5-benzothiazepine-5-acetate (1 g) obtained in Reference Example 4 in methanol (20 ml) are added potassium cyanide (0.32 g), N-(4-formylbutyl)phthalimide (1.1 g) and acetic acid (0.3 g). After being stirred overnight at room temperature, the mixture is concentrated to dryness under reduced pressure to give tert-butyl 3(R)-(1-cyano-5-phthalimidopentyl)amino-4-oxo-2,3,4,5-tetrahydro-1,5-benzothiazepine-5-acetate. This crude product is used as a starting material of Reference Example 37 without further purification.

REFERENCE EXAMPLE 37

A mixture of tert-butyl 3(R)-(1-cyano-5-phthalimidopentyl)amino-4-oxo-2,3,4,5-tetrahydro-1,5-benzothiazepine-5-acetate (2 g) obtained in Reference Example 36 and ethanolic hydrogen chloride (11N, 20 ml) is stirred for 6 hours at ice bath temperature and then allowed to stand overnight at room temperature. After evaporation of ethanol, Amberlyst 15 ion-exchange resin (10 g) and ethanol (50 ml) are added to the residue, and the resulting mixture is refluxed for 7 hours with stirring. After cooling, a portion of the ion-exchange resin is treated with 5% pyridine-ethanol solution. The eluate and ethanol layer are combined and concentrated under reduced pressure. The oily residue is dissolved in ethyl acetate (300 ml), and the solution is washed successively with 0.1N hydrochloric acid and water, dried over anhydrous magnesium sulfate and concentrated under reduced pressure. The residue is purified by silica gel column chromatography eluting with hexane-acetone (2:1) to give ethyl 3(R)-(1-ethoxycarbonyl-5-phthalimidopentyl)amino-4-oxo-2,3,4,5-tetrahydro-1,5-benzothiazepine-5-acetate (0.9 g) as colorless oil.

IR $\nu_{max}^{neat}$ cm$^{-1}$: 1770, 1740, 1720, 1710 (phthalimido and ester), 1670 (amido).

Mass spectrum (m/e): 567(M+).

REFERENCE EXAMPLE 38

To a solution of tert-butyl 3(R)-amino-4-oxo-2,3,4,5-tetrahydro-1,5-benzothiazepine-5-acetate (1 g) obtained in Reference Example 4 and 2(S)-benzyloxycarbonylamino-3-phenylpropionaldehyde (1 g) in methanol (20 ml) are added potassium cyanide (0.35 g) and acetic acid (0.3 g). After stirring overnight at room temperature, 2(S)-benzyloxycarbonylamino-3-phenylpropionaldehyde (0.4 g), potassium cyanide (0.2 g) and acetic acid (0.2 g) are added to the mixture, and stirring is continued for 3 days. The mixture is concentrated to dryness under reduced pressure to give tert-butyl 3(R)-[2(S)-benzyloxycarbonylamino-1-cyano-3-phenylpropyl]amino-4-oxo-2,3,4,5-tetrahydro-1,5-benzothiazepine-5-acetate. This crude product is used as a starting material of Reference Example 39 without further purification.

REFERENCE EXAMPLE 39

A mixture of tert-butyl 3(R)-[2(S)-benzyloxycarbonylamino-1-cyano-3-phenylpropyl]amino-4-oxo-2,3,4,5-tetrahydro-1,5-benzothiazepine-5-acetate obtained in Reference Example 38 and ethanolic hydrogen chloride (11N, 20 ml) is stirred overnight at room temperature. After evaporation of the solvent, ethanol (50 ml) and Amberlyst 15 ion-exchange resin (10 g) are added to the residue, and the resulting mixture is stirred under reflux for 9 hours. After filtration, a portion of the ion-exchange resin is eluted with a mixture of ammonia water-ethanol (1:9), and the eluate is concentrated reduced pressure. Ethyl acetate (100 ml), water (50 ml) and potassium carbonate (1 g) are added to the residue, and to the resulting mixture is added dropwise benzyloxycarbonyl chloride (1 ml) at room temperature with stirring. After stirring for 1.5 hours, ethyl acetate layer is washed with water and concentrated under reduced pressure to give an oily residue, which is purified with silica gel column chromatography using hexane:acetone (3:1–1:1) as an eluant to yield ethyl 3(R)-[2(S)-benzyloxycarbonylamino-1-ethoxycarbonyl-3-phenylpropyl]amino-4-oxo-2,3,4,5-tetrahydro-1,5-benzothiazepine-5-acetate (0.22 g) as a colorless oil.

IR $\nu_{max}^{neat}$ cm$^{-1}$: 3350(NH); 1720, 1680 (C=O).

Mass spectrum (m/e): 619(M+).

REFERENCE EXAMPLE 40

To a solution of 3(R)-phthalimido-2,3-dihydro-1,5(5H)-benzothiazepin-4-one (6.48 g) obtained in Reference Example 2 in N,N-dimethylformamide (25 ml) are added tert-butyl 2-bromopropionate (6.27 g), potassium carbonate (5.5 g) and potassium iodide (0.5 g). The resulting mixture is stirred overnight at room temperature, diluted with water (200 ml) and extracted with ethyl acetate (300 ml). The extract is washed successively with 0.5N hydrochloric acid (200 ml) and saturated aqueous sodium bicarbonate (100 ml), dried over anhydrous magnesium sulfate and concentrated under reduced pressure. The oily residue is chromatographed on silica gel using hexane-ethyl acetate (3:1–2:1) as an eluant to give tert-butyl 3(R)-phthalimido-4-oxo-2,3,4,5-tetrahydro-1,5-benzothiazepine-5-α-methylacetate (7.8 g) as colorless powder.

IR $\nu_{max}^{neat}$ cm$^{-1}$: 1770, 1730, 1720, 1680 (C=O).

Elemental analysis, for $C_{24}H_{24}N_2O_5S \cdot 1/2H_2O$; Calcd.: C, 62.46; H, 5.46; N, 6.07; Found: C, 62.62; H, 5.14; N, 6.13.

REFERENCE EXAMPLE 41

Seven point six g of tert-butyl 3(R)-phthalimido-4-oxo-2,3,4,5-tetrahydro-1,5-benzothiazepine-5-α-methylacetate obtained in Reference Example 40 is treated with hydrazine hydrate in a manner similar to that described in Reference Example 4 to give tert-butyl 3(R)-amino-4-oxo-2,3,4,5-tetrahydro-1,5-benzothiazepine-5-α-methylacetate (5.4 g) as a pale yellow oil.

IR $\nu_{max}^{neat}$ cm$^{-1}$: 1735, 1670 (C=O).

$[\alpha]_D$ —223° (c=0.5, in methanol).

Mass spectrum (m/e): 322(M+).

REFERENCE EXAMPLE 42

To a solution of tert-butyl 3(R)-amino-4-oxo-2,3,4,5-tetrahydro-1,5-benzothiazepine-5-acetate (3.08 g) obtained in Reference Example 4 in N,N-dimethylformamide (20 ml) are added ethyl 2-bromo-6-phthalimidohexanoate (7.36 g), potassium carbonate (2.76 g) and potassium iodide (1.66 g). After stirring overnight at room temperature, ethyl 2-bromo-6-phthalimidohexanoate (3.68 g) and potassium carbonate (1.38 g) are added, and stirring is continued for 3 days. The mixture is diluted with water (100 ml) and extracted with ethyl acetate (300 ml). The extract is washed with water and concentrated under reduced pressure. The oily residue is dissolved in a mixture of oxalic acid (5 g) and ethyl acetate (30 ml). The solution is diluted with petroleum ether (120 ml) and agitated thoroughly. After standing, the supernatant layer is removed by decantation. This treatment with oxalic acid followed by dilution and decantation is repeated 4 times. The resulting residue is added to a mixture of saturated aqueous sodium bicarbonate (100 ml) and ethyl acetate (300 ml). The ethyl acetate layer is separated, dried over anhydrous magnesium sulfate and concentrated under reduced pressure. The oily residue is purified by chromatography on silica gel using hexane-acetone (4:1) as an eluant to give tert-butyl 3(R)-[1(R)-ethoxycarbonyl-5-phthalimidopentyl]amino-4-oxo-2,3,4,5-tetrahydro-1,5-benzothiazepine-5-acetate (1.75 g) as an oil from the first fraction.

IR $\nu_{max}^{neat}$ cm$^{-1}$: 3330 (NH); 1780, 1740, 1720, 1680 (C=O).

Mass spectrum (m/e): 595(M+).

From the second fraction tert-butyl 3(R)-[1(S)-ethoxycarbonyl-5-phthalimidopentyl]amino-4-oxo-2,3,4,5-tetrahydro-1,5-benzothiazepine-5-acetate (2.5 g) as an oil.

IR $\nu_{max}^{neat}$ cm$^{-1}$: 3330(NH); 1770, 1740, 1720, 1680 (C=O).

Mass spectrum (m/e): 595(M+).

$[\alpha]_D - 119°$ (c=0.3, in methanol).

REFERENCE EXAMPLE 43

A mixture of tert-butyl 3(R)-[1(S)-ethoxycarbonyl-5-phthalimidopentyl]amino-4-oxo-2,3,4,5-tetrahydro-1,5-benzothiazepine-5-acetate (0.2 g) obtained in Reference Example 42 and hydrogen chloride-ethyl acetate solution (5N, 5 ml) is allowed to stand at room temperature for 3 hours. Ethyl ether (50 ml) is added to the mixture to precipitate 3(R)-[1(S)-ethoxycarbonyl-5-phthalimidopentyl]-amino-4-oxo-2,3,4,5-tetrahydro-1,5-benzothiazepine-5-acetic acid hydrochloride, which is triturated with ethyl ether (100 ml) to yield colorless powder (0.13 g).

Elemental analysis, for $C_{27}H_{29}N_3O_7S\cdot HCl\cdot 1/2H_2O$; Calcd.: C, 55.42; H, 5.34; N, 7.18; Found: C, 55.09; H, 5,12; N, 7.15.

$[\alpha]_D - 114°$ (c=0.5 in methanol).

REFERENCE EXAMPLE 44

A mixture of tert-butyl 3(R)-[1(R)-ethoxycarbonyl-5-phthalimidopentyl]amino-4-oxo-2,3,4,5-tetrahydro-1,5-benzothiazepine-5-acetate (1.6 g) obtained in Reference Example 42, ethanol (20 ml) and 85% hydrazine hydrate (0.8 g) is allowed to stand overnight at room temperature. The mixture is diluted with water (200 ml) and extracted with ethyl acetate (200 ml). The ethyl acetate layer is washed successively with 0.1N aqueous sodium hydroxide and water, to give a solution of tert-butyl 3(R)-[5-amino-1(R)-ethoxycarbonylpentyl]amino-4-oxo-2,3,4,5-tetrahydro-1,5-benzothiazepine-5-acetate in ethyl acetate. A mixture of sodium bicarbonate (1.6 g) and water (50 ml) is added to this solution. To the resulting mixture is added dropwise a solution of di-tert-butyl dicarbonate (0.9 g) in ethyl acetate (5 ml) with stirring at room temperature. After stirring for 30 minutes, ethyl acetate layer is separated, dried over anhydrous magnesium sulfate and concentrated under reduced pressure. The oily residue is subjected to column chromatography using hexane-acetone (4:1) as an eluant to yield tert-butyl 3(R)-[5-tert-butoxycarbonylamino-1(R)-ethoxycarbonylpentyl]amino-4-oxo-2,3,4,5-tetrahydro-1,5-benzothiazepine-5-acetate (1.4 g) as a colorless oil.

IR $\nu_{max}^{neat}$ cm$^{-1}$: 3350(NH); 1740, 1710, 1680 (C=O).

Mass spectrum(m/e): 565(M+).

REFERENCE EXAMPLE 45

Two point six g of tert-butyl 3(R)-[1(S)-ethoxycarbonyl-5-phtalimidopentyl]amino-4-oxo-2,3,4,5-tetrahydro-1,5-benzothiazepine-5-acetate obtained in Reference Example 42 is treated successively with hydrazine hydrate and di-tert-butyl dicarbonate in a manner similar to that described in Reference Example 44. Purification by silicagel column chromatography gives tert-butyl 3(R)-[5-tert-butoxycarbonylamino-1(S)-ethoxycarbonylpentyl]amino-4-oxo-2,3,4,5-tetrahydro-1,5-benzothiazepine-5-acetate (1.87 g) as a colorless oil.

IR $\nu_{max}^{neat}$ cm$^{-1}$: 3350(NH); 1740, 1710, 1670 (C=O).

Mass spectrum(m/e): 565(M+).

$[\alpha]_D - 136°$ (c=0.8, in methanol).

REFERENCE EXAMPLE 46

A mixture of tert-butyl 3(R)-[5-tert-butoxycarbonylamino-1(S)-ethoxycarbonylpentyl]amino-4-oxo-2,3,4,5-tetrahydro-1,5-benzothiazepine-5-acetate (0.6 g) obtained in Reference Example 45, methanol (40 ml), 1N aqueous sodium hydroxide (25 ml) and water (10 ml) is stirred for 2 hours at room temperature. After evaporation of methanol, the mixture is acidified slightly with phosphoric acid and extracted with ethyl acetate. The extract is dried over anhydrous magnesium sulfate and concentrated under reduced pressure to yield tert-butyl 3(R)-[5-tert-butoxycarbonylamino-1(S)-carboxypentyl]amino-4-oxo-2,3,4,5-tetrahydro-1,5-benzothiazepine-5-acetate (0.37 g) as a colorless viscous substance, which is triturated with ethyl acetate to give colorless crystals, m.p. 134°–135° C.

Elemental analysis, for $C_{26}H_{39}N_3O_7S$; Calcd.: C,58.08; H, 7.31; N, 7.82; Found: C,58.11; H, 7.22; N, 7.73.

IR $\nu_{max}^{nujol}$ cm$^{-1}$: 3350(NH), 1730, 1700, 1680 (C=O).

REFERENCE EXAMPLE 47

A mixture of tert-butyl 3(R)-amino-4-oxo-2,3,4,5-tetrahydro-1,5-benzothiazepine-5-acetate (5 g) obtained in Reference Example 4, ethyl 2-bromo-6-phthalimidohexanoate (17.9 g), acetonitrile (200 ml) and triethylamine (2.46 g) is heated under reflux for 45 hours. After evaporation of acetonitrile, water (200 ml) and ethyl acetate (300 ml) is added to the residue, followed by extraction. The ethyl acetate layer is washed with water, dried over anhydrous magnesium sulfate and concentrated under reduced pressure. The oily residue is chromatographed on silica gel using hexane-acetone (4:1) as an eluant to yield tert-butyl 3(R)-[1(R)-ethoxycarbonyl-5-phthalimidopentyl]amino-4-oxo-2,3,4,5-tetrahydro-1,5-benzothiazepine-5-acetate (3.9 g) and tert-butyl 3(R)-[1(S)-ethoxycarbonyl-5-phthalimidopentyl]amino-4-oxo-2,3,4,5-tetrahydro-1,5-benzothiazepine-5-acetate (4.1 g). Both of products are obtained as colorless oils, which are identical with the compounds obtained in Reference Example 42.

REFERENCE EXAMPLE 48–50

Reacting tert-butyl 3(R)-amino-4-oxo-2,3,4,5-tetrahydro-1,5-benzothiazepine-5-acetate with α-bromo ester as shown in Table 7 in a manner similar to that described in Reference Example 47 to give the derivatives of benzothiazepine as shown in Table 7.

TABLE 7

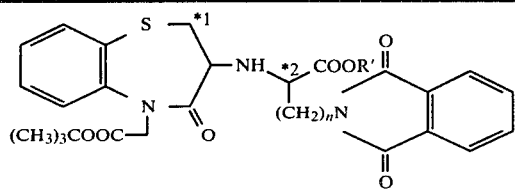

| Ref. Ex. No. | α-Bromoester used | R' | n | Config. *1 | *2 | Ir $\nu_{max}^{neat}$ cm$^{-1}$ |
|---|---|---|---|---|---|---|
| 48 | ![structure] N—(CH₂)₄CHCOO(CH₂)₃CH₃, Br | (CH₂)₃CH₃ | 4 | R | R | 3330, 1770, 1740, 1710, 1675 |
|  |  |  |  | R | R | 3320, 1770, 1740, 1710, 1670 |
| 49 | ![structure] N—(CH₂)₂CHCOOC₂H₅, Br | C₂H₅ | 2 | R | RS* | 3320, 1770, 1740, 1710, 1670 |

REFERENCE EXAMPLES 51-53

The derivatives of benzothiazepine obtained in Reference Examples 48-50 are treated with hydrogen chloride in a manner similar to that described in Reference Example 43 to give the compounds as shown in Table 8.

TABLE 8

[structure with HOOC, S, NH, COOR'', (CH₂)ₙ-N, ·HCl]

| Ref. Ex. No. | R'' | n | Config. *1 | *2 | [α]$_D$ (in methanol) |
|---|---|---|---|---|---|
| 51 | (CH₂)₃CH₃ | 4 | R | S | −106° (c = 0.6) |
| 52 | C₂H₅ | 2 | R | RS* | −133° (c = 0.5) |
| 53 | C₂H₅ | 6 | R | RS* | −105° (c = 0.5) |

*mixture of diastereomers

REFERENCE EXAMPLES 54-56

The derivatives of benzothiazepine obtained in Reference Examples 48-50 are in a manner similar to that described in Reference Example 44, allowed to react respectively with hydrazine hydrate, followed by reaction with di-tert-butyl dicarbonate to give the compounds as shown in Table 9.

TABLE 9

[structure with (CH₃)₃COOC, S, NH, COOR''', (CH₂)ₙNHCOOC(CH₃)₃]

| Ref. Ex. No. | R''' | n | Config. *1 | *2 | IR $\nu_{max}^{neat}$ cm$^{-1}$ |
|---|---|---|---|---|---|
| 54 | (CH₂)₃CH₃ | 4 | R | RS | 3350, 1730, 1710, 1670 |
| 56 | C₂H₅ | 2 | R | RS* | 3400, 1740, 1710, 1670 |
| 57 | C₂H₅ | 6 | R | RS* | 3350, 1730, 1710, 1670 |

*mixture of diastereomers

REFERENCE EXAMPLE 57

Two g of tert-butyl 3(R)-amino-4-oxo-2,3,4,5-tetrahydro-1,5-benzothiazepine-5-acetate is reacted with 7.1 g of ethyl 2-bromo-11-phthalimidoundecanate in a manner similar to that described in Reference Example 47. The obtained product is purified by silicagel column chromatography (hexane:ethyl acetate=3:1). The first fraction gives tert-butyl 3(R)-[1(R)-ethoxycarbonyl-10-phthalimidodecyl]-amino-4-oxo-2,3,4,5-tetrahydro-1,5-benzothiazepine-5-acetate (1.2 g) as a colorless oil.

IR $\nu_{max}^{neat}$ cm$^{-1}$: 3320(NH), 1770, 1740, 1710, 1680(C=O).

[α]$_D$ −104° (c=0.5 in methanol).

The second fraction gives tert-butyl 3(R)-[1(S)-ethoxycarbonyl-10-phthalimidodecyl]amino-4-oxo-2,3,4,5-tetrahydro-1,5-benzothiazepine-5-acetate (1.2 g) as a colorless oil.

IR $\nu_{max}^{neat}$ cm$^{-1}$: 3320(NH), 1770, 1740, 1710, 1670(C=O).

[α]$_D$ −113° (c=0.5 in methanol).

REFERENCE EXAMPLE 58

Zero point five g of tert-butyl 3(R)-[1(S)-ethoxycarbonyl-10-phthalimidodecyl]amino-4-oxo-2,3,4,5-tetrahydro-1,5-benzothiazepine-5-acetate is treated with hydrazine and then is reacted with di-tert-butyl dicarbonate in a manner similar to that described in Reference Example 44. The product is purified by silica gel column chromatography (hexane:ethyl acetate=2:1) to provide tert-butyl 3(R)-[10-tert-butoxycarbonylamino-1(S)-ethoxycarbonyldecyl]amino-4-oxo-2,3,4,5-tetrahydro-1,5-benzothiazepine-5-acetate (0.35 g) as a colorless oil.

IR $\nu_{max}^{neat}$ cm$^{-1}$: 3400(NH), 1740, 1710, 1670(C=O).

$[\alpha]_D$ −127° (c=0.7 in methanol).

EXAMPLE 1

A mixture of 50 ml of ethanol, 1.5 g of tert-butyl 3(R)-amino-4-oxo-2,3,4,5-tetrahydro-1,5-benzothiazepine-5-acetate obtained in Reference Example 4, 0.3 g of acetic acid, 4.2 g of ethyl 2-oxo-4-phenyl butyrate and 8 g of molecular sieve 4A is stirred at room temperature for 30 minutes. A solution of 0.6 g of sodium cyanoborohydride in 40 ml of ethanol is added dropwise to the mixture at room temperature over a period of 2 hours. After stirring at room temperature overnight, 2.1 g of ethyl 2-oxo-4-phenylbutyrate is added to the mixture. To the resulting mixture is added dropwise a solution of 1.3 g of sodium cyanoborohydride in 40 ml of ethanol over a period of 2 hours. The mixture is concentrated under reduced pressure, diluted with 100 ml of water and extracted with 200 ml of ethyl acetate. The insoluble substance is removed by filtration, and the ethyl acetate layer is dried over anhydrous magnesium sulfate and concentrated under reduced pressure. After 50 ml of ethyl ether and 2 g of oxalic acid are added to the residue, the mixture is shaken thoroughly and diluted with 300 ml of petroleum ether. The resulting mixture is allowed to stand overnight. The supernatant layer is removed by decantation, and 50 ml of water, 300 ml of ethyl acetate are added to the precipitate, followed by neutralization with an excess of sodium bicarbonate. The ethyl acetate layer is dried over anhydrous magnesium sulfate and concentrated under reduced pressure to give an oily residue, which is separated and purified by silica gel column chromatography (hexane:ethyl acetate=5:1-10:3) to yield firstly 0.55 g of tert-butyl 3(R)-[1(R)-ethoxycarbonyl-3-phenylpropyl]amino-4-oxo-2,3,4,5-tetrahydro-1,5-benzothiazepine-5-acetate as an oil.

IR $\nu_{max}^{neat}$ cm$^{-1}$: 3320(NH), 1730(ester), 1670(amide).

Elemental analysis, for C$_{27}$H$_{34}$N$_2$O$_5$S; Calcd.: C, 65.04; H, 6.87; N, 5.62; Found: C, 65.36; H, 6.91; N, 5.61.

From the succeeding fraction, 0.4 g of a mixture of the above-mentioned tert-butyl 3(R)-[1(R)-ethoxycarbonyl-3-phenylpropyl]amino-4-oxo-2,3,4,5-tetrahydro-1,5-benzothiazepine-5-acetate and the below-described tert-butyl 3(R)-[1(S)-ethoxycarbonyl-3-phenylpropyl]amino-4-oxo-2,3,4,5-tetrahydro-1,5-benzothiazepine-5-acetate, namely a mixture of two diastereomers, is obtained as an oil. The ratio of the diastereomers is about 1:1.

From the subsequently succeeding fraction, 0.75 g of pure tert-butyl 3(R)-[1(S)-ethoxycarbonyl-3-phenylpropyl]-amino-4-oxo-2,3,4,5-tetrahydro-1,5-benzothiazepine-5-acetate is obtained as a colorless oil.

IR $\nu_{max}^{neat}$ cm$^{-1}$: 3320(NH), 1740(ester), 1670(amide).

Elemental analysis, for C$_{27}$H$_{34}$N$_2$O$_5$S; Calcd.: C, 65.04; H, 6.87; N, 5.62; Found: C, 64.90; H, 6.63; N, 5.66.

EXAMPLE 2

In a manner similar to that described in Example 1, the reaction of 1.5 g of tert-butyl 3(R)-amino-4-oxo-2,3,4,5-tetrahydro-1,5-benzothiazepine-5-acetate with 5 g of ethyl 4-cyclohexyl-2-oxobutyrate obtained in Reference Example 5 is carried out, and the product is purified by silica gel column chromatography (hexane:ethyl acetate=4:1). From the first fraction is obtained 0.3 g of tert-butyl 3(R)-[1(R)-ethoxycarbonyl-3-cyclohexylpropyl]amino-4-oxo-2,3,4,5-tetrahydro-1,5-benzothiazepine-5-acetate as a colorless oil.

IR $\nu_{max}^{neat}$ cm$^{-1}$: 3320(NH), 1730(ester), 1670(amide).

From the second fraction, 0.45 g of tert-butyl 3(R)-[1(S)-ethoxycarbonyl-3-cyclohexylpropyl]amino-4-oxo-2,3,4,5-tetrahydro-1,5-benzothiazepine-5-acetate is obtained as a colorless oil.

IR $\nu_{max}^{neat}$ cm$^{-1}$: 3320(NH), 1730(ester), 1670(amide).

EXAMPLE 3

A mixture of 50 ml of ethanol, 1 g of tert-butyl 3(R)-amino-4-oxo-2,3,4,5-tetrahydro-1,5-benzothiazepine-5-acetate, 0.4 g of acetic acid, 3.6 g of ethyl 4-(p-methylphenyl)-2-oxobutyrate and 5 g of molecular sieve 4A is stirred at room temperature for 1 hour, and the mixture is subjected to catalytic reduction over 0.5 g of 5% palladium carbon, at ordinary temperature and at atmospheric pressure. After 7 hours, the catalyst is filtered off and the mixture is concentrated. The residue is treated with oxalic acid in a manner similar to that described in Example 1. The resulting oil is purified by silica gel column chromatography to give 0.3 g of tert-butyl 3(R)-[1-ethoxycarbonyl-3-(p-tolyl)propyl]amino-4-oxo-2,3,4,5-tetrahydro-1,5-benzothiazepine-5-acetate as colorless oil. This product is a mixture of two diastereomers (about 1:1).

IR $\nu_{max}^{neat}$ cm$^{-1}$: 3320(NH), 1730(ester), 1670(amide).

EXAMPLE 4

The reaction of 1 g of tert-butyl 3(R)-amino-4-oxo-2,3,4,5-tetrahydro-1,5-benzothiazepine-5-acetate with 4 g of isobutyl 2-oxo-3-phenylbutyrate is carried out similarly to the case of Example 3 to yield 0.45 g of tert-butyl 3(R)-[1-isobutoxycarbonyl-3-phenylpropyl]amino-4-oxo-2,3,4,5-tetrahydro-1,5-benzothiazepine-5-acetate as colorless oil.

IR $\nu_{max}^{neat}$ cm$^{-1}$: 3330(NH), 1730(ester), 1670(amide).

EXAMPLE 5

A mixture of 5 ml of 5N hydrogen chloride-ethyl acetate solution and 0.5 g of tert-butyl 3(R)-[1(R)-ethoxycarbonyl-3-phenylpropyl]amino-4-oxo-2,3,4,5-tetrahydro-1,5-benzothiazepine-5-acetate obtained in Example 1 is allowed to stand at room temperature overnight. Twenty ml of ether and 100 ml of petroleum ether are added to the mixture to deposit colorless powder, which is collected by filtration to give 0.42 g of 3(R)-[1(R)-ethoxycarbonyl-3-phenylpropyl]amino-4-oxo-2,3,4,5-tetrahydro-1,5-benzothiazepine-5-acetic acid hydrochloride.

Elemental analysis, for $C_{23}H_{26}N_2O_5S\cdot HCl$; Calcd.: C, 57.68; H, 5.68; N, 5.85; Found: C, 57.53; H, 5.76; N, 5.70. $[\alpha]_D^{22} -173°$ (c=1, in methanol).

EXAMPLES 6-11

The tert-butyl 1,5-benzothiazepine-5-acetate derivatives obtained in Examples 1-4 are treated with hydrogen chloride in a manner similar to that described in Example 5 to give the compounds as shown in Table 10.

TABLE 10

| Ex. No. | $R_9$ | $R_{10}$ | Config. *1 | Config. *2 | $[\alpha]_D$ (in methanol) |
|---|---|---|---|---|---|
| 6 | $C_2H_5$ | ⟨phenyl⟩ | R | R,S* | −134° (c = 1) |
| 7 | $C_2H_5$ | ⟨phenyl⟩ | R | S | −117° (c = 0.7) |
| 8 | $C_2H_5$ | ⟨H-phenyl⟩ | R | R | −161° (c = 0.9) |
| 9 | $C_2H_5$ | ⟨H-phenyl⟩ | R | S | −125° (c = 0.7) |
| 10 | $C_2H_5$ | ⟨phenyl⟩-CH3 | R | R,S* | −138° (c = 0.9) |
| 11 | $CH_2CH(CH_3)_2$ | ⟨phenyl⟩ | R | R,S* | −117° (c = 1) |

*mixture of diastereomers

EXAMPLE 12

A mixture of 1 ml of ethanol, 3 ml of 1N aqueous sodium hydroxide and 0.1 g of 3(R)-[1(R)-ethoxycarbonyl-3-phenylpropyl]-amino-4-oxo-2,3,4,5-tetrahydro-1,5-benzothiazepine-5-acetic acid hydrochloride obtained in Example 5 is allowed to stand at room temperature for 10 minutes and then in a refrigerator for 30 minutes. The deposited colorless plates are collected by filtration to give 0.05 g of 3(R)-[1(R)-carboxy-3-phenylpropyl]amino-4-2,3,4,5-tetrahydro-1,5-benzothiazepine-5-acetic acid disodium salt, m.p. 215°–220° C.

IR $\nu_{max}^{neat}$ cm$^{-1}$: 1660(amide), 1600(carboxylate).

Elemental analysis, for $C_{21}H_{20}N_2Na_2O_5S\cdot 5/2H_2O$; Calcd.: C, 50.10; H, 5.00; N, 5.56; Found: C, 50.28; H, 5.29; N, 5.91.

EXAMPLE 13

A mixture of 2 ml of ethanol, 6 ml of 1N aqueous sodium hydroxide and 0.2 g of 3(R)-[1(S)-ethoxycarbonyl-3-phenylpropyl]amino-4-oxo-2,3,4,5-tetrahydro-1,5-benzothiazepine-5-acetic acid obtained in Example 7 is allowed to stand at room temperature for 30 minutes and concentrated under reduced pressure at room temperature to about 1 ml. The concentrated solution is acidified slightly with acetic acid, and the deposited colorless prisms are collected by filtration to yield 0.134 g of 3(R)-[1(S)-carboxy-3-phenylpropyl]amino-4-oxo-2,3,4,5-tetrahydro-1,5-benzothiazepine-5-acetic acid monosodium salt, m.p. 166°–169° C.

IR $\nu_{max}^{neat}$ cm$^{-1}$: 1720(carboxylic acid), 1670(amide), 1640(carboxylate).

$[\alpha]_D^{22} -122°$ [c=0.2 (methanol:water=1:1)].

EXAMPLES 14-17

In a manner similar to that described in Example 1, the tert-butyl aminobenzothiazepine-acetate derivatives obtained in Reference Examples 23-26 are allowed to react with ethyl 2-oxo-4-phenylbutyrate to give the compounds shown in Table 11 as an oil.

TABLE 11

| Ex. No. | R | Config. *1 | Config. *2 | IR $\nu_{max}^{neat}$(cm$^{-1}$) | Mass spectrum m/e (M$^+$) |
|---|---|---|---|---|---|
| 14 | 7-$CH_3$ | R | R | 1675 (amide), 1740 (ester) | 512 |
|  |  | R | S | 1675 (amide), 1740 (ester) | 512 |
| 15 | 7-$OCH_3$ | R | R | 1660 (amide), 1720 (ester) | 528 |
|  |  | R | S | 1660 (amide), 1730 (ester) | 528 |
| 16 | 7,8-$(CH_2)_3$— | R | RS* | — | 538 |
|  |  | R | R | 1680 (amide), 1740 (ester) | 532 |
| 17 | 7-Cl | R | S | 1680 (amide), 1740 (ester) | 532 |

*mixture of diastereomers

EXAMPLES 18-24

The 1-ethoxycarbonyl-3-phenylpropylaminobenzothiazepine derivatives obtained in Examples 14-17 are treated with hydrogen chloride in a manner similar to that described in Example 5 to give the compounds shown in Table 12 as colorless powder.

TABLE 12

| Ex. No. | R | Config. *1 | Config. *2 | $[\alpha]_D$ (in methanol) |
|---|---|---|---|---|
| 18 | 7-$CH_3$ | R | R | −161° |
| 19 | 7-$CH_3$ | R | S | −107° |
| 20 | 7-$OCH_3$ | R | R | −138° |
| 21 | 7-$OCH_3$ | R | S | −94° |
| 22 | 7,8-$(CH_2)_3$— | R | R,S* | −113° |
| 23 | 7-Cl | R | R | −145° |
| 24 | 7-Cl | R | S | −99° |

*mixture of diastereomers

EXAMPLES 25-29

In a manner similar to that described in Example 1, tert-butyl 3(R)-amino-4-oxo-2,3,4,5-tetrahydro-1,5-benzothiazepine-5-acetate obtained in Reference Example 4 is allowed to react with the α-keto esters obtained in Reference Examples 27-30 or ethyl pyruvate to give the compounds shown in Table 13 as an oil.

TABLE 13

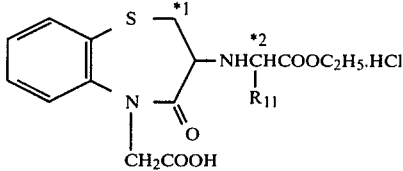

| Ex. No. | $R_{11}$ | Config. *1 | *2 | IR $\nu_{max}^{neat}$ (cm$^{-1}$) | Mass spectrum m/e (M$^+$) |
|---|---|---|---|---|---|
| 25 | —(CH$_2$)$_7$CH$_3$ | R | R,S* | 1680 (amide) 1730 (ester) | 506 |
| 26 | —CH$_2$CH(C$_6$H$_5$)$_2$ | R | R,S* | 1680 (amide) 1740 (ester) | 574 |
|  | —(CH$_2$)$_2$CH(CH$_3$)$_2$ | R | R | 1680 (amide) 1740 (ester) | 464 |
| 27 | —(CH$_2$)$_2$CH(CH$_3$)$_2$ | R | S | 1670 (amide) 1730 (ester) | 464 |
| 28 | —(CH$_2$)$_2$-cyclohexyl | R | R,S* | 1680 (amide) 1740 (ester) | 518 |
| 29 | CH$_3$ | R | R,S* | 1670 (amide) 1740 (ester) | 408 |

*mixture of diastereomers

EXAMPLES 30-35

The tert-butyl 1,5-benzothiazepine-5-acetate derivatives obtained in Examples 25-29 are treated with hydrogen chloride in a manner similar to that described in Example 5 to give the compounds shown in Table 14 as colorless powder.

TABLE 14

| Ex. No. | $R_{11}$ | Config. *1 | *2 | $[\alpha]_D$ (in methanol) |
|---|---|---|---|---|
| 30 | —(CH$_2$)$_7$CH$_3$ | R | R,S* | −132° |

TABLE 14-continued

| Ex. No. | $R_{11}$ | Config. *1 | *2 | $[\alpha]_D$ (in methanol) |
|---|---|---|---|---|
| 31 | —CH$_2$CH(C$_6$H$_5$)$_2$ | R | R,S* | −103° |
| 32 | —(CH$_2$)$_2$CH(CH$_3$)$_2$ | R | R | −175° |
| 33 | —(CH$_2$)$_2$CH(CH$_3$)$_2$ | R | S | −150° |
| 34 | —(CH$_2$)$_2$-cyclohexyl(CH$_3$) | R | R,S* | −145° |
| 35 | —CH$_3$ | R | R,S* | −119° |

*mixture of diastereomers

EXAMPLE 36

A mixture of 50 ml of ethanol, 0.65 g of 3(R)-amino-4-oxo-7-trifluoromethyl-2,3,4,5-tetrahydro-1,5-benzothiazepine-5-acetic acid hydrobromide obtained in Reference Example 34, 0.2 g of sodium acetate, 0.19 g of acetic acid, 1.67 g of ethyl 2-oxo-4-phenylbutyrate and 5 g of molecular sieve 4A is stirred at room temperature for 1 hour. A solution of 0.56 g of sodium cyanoborohydride in ethanol is added dropwise to the mixture over a period of 2 hours. The solvent is evaporated off under reduced pressure, and 50 ml of water and 150 ml of ethyl acetate are added to the residue. After the insoluble substance is filtered off, the ethyl acetate layer is dried over anhydrous magnesium sulfate and concentrated under reduced pressure. The residue is dissolved in a mixture of ether and petroleum ether, and hydrogen chloride-ethyl acetate solution is added to the solution to deposit 0.7 g of 3(R)-[1-ethoxycarbonyl-3-phenylpropyl]amino-4-oxo-7-trifluoromethyl-2,3,4,5-tetrahydro-1,5-benzothiazepine-5-acetic acid hydrochloride as colorless powder.

$[\alpha]_D$ −95° (in methanol).

Mass spectrum (m/e): 510(M$^+$).

EXAMPLE 37

A mixture of 10 ml of N,N-dimethylformamide, 0.3 g of 3(R)-[1(S)-ethoxycarbonyl-3-phenylpropyl]amino-4-oxo-2,3,4,5-tetrahydro-1,5-benzothiazepine-5-acetic acid hydrochloride obtained in Example 7, 1 g of sodium bicarbonate and 0.15 g of benzyl bromide is stirred at room temperature overnight. The mixture is diluted with 100 ml of water and extracted with 200 ml of ethyl acetate. The extract is washed successively with water, aqueous sodium bicarbonate, water, 0.1N hydrochloric acid and water and dried over anhydrous magnesium sulfate. The ethyl acetate is evaporated under reduced pressure, and the oily residue is dissolved in 30 ml of ether. The solution is treated with 0.5 ml of hydrogen chloride-ethyl acetate solution (5N) to deposit 0.25 g of benzyl 3(R)-[1(S)-ethoxycarbonyl-3-phenylpropyl]amino-4-oxo-2,3,4,5-tetrahydro-1,5-benzothiazepine-5-acetate hydrochloride as colorless powder.

Elemental analysis, for $C_{30}H_{32}N_2O_5S.HCl$; Calcd.: C, 63.31; H, 5.84; N, 4.92; Found: C, 63.02; H, 5.82; N, 5.19.

Mass spectrum (m/e): 532(M+).

$[\alpha]_D$ −90° (in methanol).

EXAMPLE 38

A solution of 0.1 g of benzyl 3(R)-[1(S)-ethoxycarbonyl-3-phenylpropyl]amino-4-oxo-2,3,4,5-tetrahydro-1,5-benzothiazepine-5-acetate hydrochloride in 10 ml of ethanol is subjected to catalytic reduction over 0.2 g of 10% palladium-carbon (containing 50% of water) at ordinary temperature and at atmospheric pressure. The catalyst is filtered off, and the filtrate is concentrated and diluted with a mixture of ether and petroleum ether to precipitate 0.05 g of 3(R)-[1(S)-ethoxycarbonyl-3-phenylpropyl]amino-4-oxo-2,3,4,5-tetrahydro-1,5-benzothiazepine-5-acetic acid hydrochloride as colorless powder, which is identical with the compound obtained in Example 7.

EXAMPLE 39

To a stirred solution of 0.5 g of 3(R)-[1(S)-ethoxycarbonyl-3-phenylpropyl]amino-4-oxo-2,3,4,5-tetrahydro-1,5-benzothiazepine-5-acetic acid hydrochloride obtained in Example 7 in 50 ml of methylene chloride is added portionwise 0.5 g of m-chloroperbenzoic acid at room temperature over a period of 2.5 hours. The resulting mixture is stirred at room temperature for 1 hour, and 200 ml of water and 50 ml of methylene chloride are added. The methylene chloride layer is washed with water, dried over anhydrous magnesium sulfate and concentrated under reduced pressure. The residue is dissolved in 100 ml of ethyl ether, and treated with 0.5 ml of hydrogen chloride-ethyl acetate solution (5N) to deposit 0.3 g of 3(R)-[1(S)-ethoxycarbonyl-3-phenylpropyl]amino-4-oxo-2,3,4,5-tetrahydro-1,5-benzothiazepine-5-acetic acid S-oxide hydrochloride as colorless powder.

Elemental analysis, for $C_{23}H_{26}N_2O_6S.HCl.H_2O$; Calcd.: C, 53.85; H, 5.70; N, 5.46; Found: C, 54.29; H, 5.70; N, 5.27.

Mass spectrum (m/e): 458 (M+).

$[\alpha]_D$ −80° (in methanol).

EXAMPLE 40

To a stirred solution of 0.5 g of 3(R)-[1(S)-ethoxycarbonyl-3-phenylpropyl]amino-4-oxo-2,3,4,5-tetrahydro-1,5-benzothiazepine-5-acetic acid hydrochloride obtained in Example 7 and 0.3 g of tert-butyl L-phenylalaninate in 10 ml of N,N-dimethylformamide is added dropwise a solution of 0.23 g of diethyl phosphorocyanidate in 2 ml of dimethylformamide at ice bath temperature. After 10 minutes a solution of 0.23 g of triethylamine in 2 ml of N,N-dimethylformamide is added dropwise to the cooled mixture, and stirring is continued for 30 minutes. The mixture was diluted with 100 ml of water, and extracted with 200 ml of ethyl acetate. The extract is washed successively with 0.02N hydrochloric acid, 0.05N aqueous sodium hydroxide and water, dried over anhydrous magnesium sulfate and concentrated under reduced pressure. The residue is dissolved in petroleum ether, and 1 ml of hydrogen chloride-ethyl acetate solution (5N) is added to the solution to precipitate 0.63 g of tert-butyl 3(R)-[1(S)-ethoxycarbonyl-3-phenylpropyl]amino-4-oxo-2,3,4,5-tetrahydro-1,5-benzothiazepin-5-yl-N-acetyl-L-phenylalaninate hydrochloride as colorless powder.

Elemental analysis, for $C_{36}H_{43}N_3O_6S.HCl.\frac{1}{2}H_2O$; Calcd.: C, 62.55; H, 6.56; N, 6.08; Found: C, 62.61; H, 6.77; N, 5.89.

Mass spectrum (m/e): 645 (M+).

$[\alpha]_D$ −79° (in methanol).

EXAMPLE 41

A mixture of 5 ml of hydrogen chloride-ethyl acetate solution (5N) and 0.45 g of tert-butyl 3(R)-[(S)-ethoxycarbonyl-3-phenylpropyl]amino-4-oxo-2,3,4,5-tetrahydro-1,5-benzothiazepin-5-yl-N-acetyl-L-phenylalaninate hydrochloride obtained in Example 40 is allowed to stand at room temperature for 3 hours and concentrated under reduced pressure. A mixture of ethyl acetate and ethyl ether is added to the residue to deposit 0.26 g of 3(R)-[1(S)-ethoxycarbonyl-3-phenylpropyl]amino-4-oxo-2,3,4,5-tetrahydro-1,5-benzothiazepin-5-yl-N-acetyl-L-phenylalanine hydrochloride as colorless crystals, m.p. 153°–157° C.

Elemental analysis, for $C_{32}H_{35}N_3O_6S.HCl$; Calcd.: C, 61.38; H, 5.79; N, 6.71; Found: C, 61.21; H, 5.78; N, 6.66.

Mass spectrum (m/e): 589 (M+).

$[\alpha]_D$ −96° (in methanol).

EXAMPLE 42

A solution of 1 g of tert-butyl 3(R)-[1(S)-ethoxycarbonyl-3-phenylpropyl]amino-4-oxo-2,3,4,5-tetrahydro-1,5-benzothiazepine-5-acetate obtained in Example 1 in 100 ml of methylene chloride is added 0.51 g of m-chloroperbenzoic acid. After stirring for 30 minutes, 0.15 g of m-chloroperbenzoic acid is added, and stirring is continued for further 30 minutes. Fifty ml of 1N aqueous sodium hydroxide is added to the mixture, and the methylene chloride layer is separated, washed with water and concentrated under reduced pressure to yield tert-butyl 3(R)-[1(S)-ethoxycarbonyl-3-phenylpropyl]amino-4-oxo-2,3,4,5-tetrahydro-1,5-benzothiazepine-5-acetate 1-oxide as a mixture of two stereoisomers. Separation by silica gel column chromatography yields 0.3 g of one isomer and 0.5 g of another isomer. Both are obtained as colorless oil. Mass spectrum of each isomer shows the peak due to molecular ion at 514.

EXAMPLE 43

A mixture of 6 ml of ethanol, 0.8 g of tert-butyl 3(R)-[1(S)-ethoxycarbonyl-3-phenylpropyl]amino-4-oxo-2,3,4,5-tetrahydro-1,5-benzothiazepine-5-acetate obtained in Example 1 and 3 ml of 1N aqueous sodium hydroxide is stirred at room temperature for 2 hours. The mixture is diluted with 200 ml of water and extracted with 100 ml of ethyl ether. The aqueous layer is acidified slightly with 1N hydrochloric acid to precipitate 0.5 g of tert-butyl 3(R)-[1(S)-carboxy-3-phenylpropyl]amino-4-oxo-2,3,4,5-tetrahydro-1,5-benzothiazepine-5-acetate as colorless crystals, m.p. 165°–167° C.

$[\alpha]_D$ −101° (in methanol).

Elemental analysis, for $C_{25}H_{30}N_2O_5S$; Calcd.: C, 63.81; H, 6.43; N, 5.95; Found: C, 63.69; H, 6.38; N, 5.87.

EXAMPLE 44

A mixture of 10 ml of N,N-dimethylformamide, 0.3 g of tert-butyl 3(R)-[1(S)-carboxy-3-phenylpropyl]amino-4-oxo-2,3,4,5-tetrahydro-1,5-benzothiazepine-5-acetate obtained in Example 43, 0.5 g of sodium bicarbonate and 0.15 g of benzyl bromide is stirred at room temperature overnight. The mixture is diluted with water (100 ml) and extracted with ethyl acetate (200 ml). The extract is washed successively with 0.1N hydrochloric acid and water, dried over anhydrous magnesium sulfate and concentrated under reduced pressure to give 0.35 g of tert-butyl 3(R)-[1(S)-benzyloxycarbonyl-3-phenylpropyl]amino-4-oxo-2,3,4,5-tetrahydro-1,5-benzothiazepine-5-acetate as a colorless oil.

IR $\nu_{max}^{neat}$ cm$^{-1}$: 3330(NH), 1740(ester), 1680(amide).

Mass spectrum (m/e): 560 (M+).

EXAMPLE 45

In a manner similar to that described in Example 5, 0.35 g of tert-butyl 3(R)-[1(S)-benzyloxycarbonyl-3-phenylpropyl]amino-4-oxo-2,3,4,5-tetrahydro-1,5-benzothiazepine-5-acetate obtained in Example 44 is treated with hydrogen chloride to give 0.25 g of 3(R)-[1(S)-benzyloxycarbonyl-3-phenylpropyl]amino-4-oxo-2,3,4,5-tetrahydro-1,5-benzothiazepine-5-acetic acid hydrochloride as colorless powder.

Elemental analysis, for $C_{28}H_{28}N_2O_5S\cdot HCl$; Calcd.: C, 62.16; H, 5.40; N, 5.18; Found: C, 61.77; H, 5.44; N, 4.96.

$[\alpha]_D - 82°$ (in methanol).

Mass spectrum (m/e): 504 (M+).

EXAMPLE 46

To a solution of 2 g of tert-butyl 3(R)-amino-4-oxo-2,3,4,5-tetrahydro-1,5-benzothiazepine-5-acetate obtained in Reference Example 4 in 20 ml of ethanol are added 1.6 g of ethyl bromoacetate and 1 g of triethylamine. After standing at room temperature overnight, the mixture is concentrated to dryness under reduced pressure, and the residue is purified by silica gel column chromatography (hexane:ethyl acetate=2:1) to yield 1.8 g of tert-butyl 3(R)-ethoxycarbonylmethylamino-4-oxo-2,3,4,5-tetrahydro-1,5-benzothiazepine-5-acetate as a colorless oil.

IR $\nu_{max}^{neat}$ cm$^{-1}$: 3330(NH), 1740(ester), 1670(amide).

Mass spectrum (m/e): 394 (M+).

EXAMPLE 47

A mixture of 15 ml of hydrogen chloride-ethyl acetate solution (5N) and 1.8 g of tert-butyl 3(R)-ethoxycarbonylmethylamino-4-oxo-2,3,4,5-tetrahydro-1,5-benzothiazepine-5-acetate is allowed to stand at room temperature for 3 hours. Fifty ml of ethyl ether is added to the mixture to precipitate 1.6 g of 3(R)-ethoxycarbonylmethylamino-4-oxo-2,3,4,5-tetrahydro-1,5-benzothiazepine-5-acetic acid hydrochloride as colorless prisms.

m.p. 223°–225° C. (decomp.)

Elemental analysis, for $C_{15}H_{18}N_2O_5S\cdot HCl$; Calcd.: C, 48.06; H, 5.11; N, 7.47; Found: C, 47.99; H, 5.11; N, 7.25.

$[\alpha]_D - 193°$ (in methanol).

Mass spectrum (m/e): 338 (M+).

EXAMPLE 48

A mixture of 20 ml of ethanol and 0.5 g of 3(R)-(N-benzyl-N-ethoxycarbonylmethylamino)-4-oxo-2,3,4,5-tetrahydro-1,5-benzothiazepine-5-acetic acid hydrochloride obtained in Reference Example 35 is catalytic reduction over 0.5 g of 10% palladium-carbon (containing 50% of moisture) as a catalyst at ordinary temperature and at atmospheric pressure. After the absorption of hydrogen stops, the catalyst is filtered off, and the filtrate is concentrated to give crystals. Ethyl acetate is added to the crystals, and the deposited substance are collected by filtration to yield 0.3 g of 3(R)-ethoxycarbonylmethylamino-4-oxo-2,3,4,5-tetrahydro-1,5-benzothiazepine-5-acetic acid as colorless prisms, m.p. 223°–226° C.

$[\alpha]_D - 171°$ (in methanol).

Mass spectrum (m/e): 338 (M+).

EXAMPLE 49

In 5 ml of 1N aqueous sodium hydroxide is dissolved 0.5 g of 3(R)-ethoxycarbonylmethylamino-4-oxo-2,3,4,5-tetrahydro-1,5-benzothiazepine-5-acetic acid hydrochloride obtained in Example 47. The solution is allowed to stand at room temperature for 3 hours, and neutralized with 1N hydrochloric acid. Purification is carried out by using Amberlite IR-45.

The desired compound is eluted with 1% aqueous ammonia, and the eluate is concentrated to dryness under reduced pressure. The residue is treated with a mixture of ethyl ether and petroleum ether to deposit colorless powder, which is collected by filtration to give 0.25 g of 3(R)-carboxymethylamino-4-oxo-2,3,4,5-tetrahydro-1,5-benzothiazepine-5-acetic acid.

Elemental analysis, for $C_{13}H_{14}N_2O_5S\cdot 2H_2O$; Calcd.: C, 45.09; H, 5.24; N, 8.09; Found: C, 45.19; H, 4.94; N, 8.03.

$[\alpha]_D - 196°$ (in water).

EXAMPLE 50

In 2 ml of methanol are dissolved 0.1 g of 3(R)-[1(S)-ethoxycarbonyl-3-cyclohexylpropyl]amino-4-oxo-2,3,4,5-tetrahydro-1,5-benzothiazepine-5-acetic acid hydrochloride and 1.5 ml of 1N aqueous sodium hydroxide. The solution is allowed to stand at room temperature for 2 hours, concentrated to about 1 ml at a temperature of not higher than 40° C. under reduced pressure, and acidified slightly with 1N hydrochloric acid to give 0.067 g of 3(R)-[1(S)-carboxy-3-cyclohexylpropyl]amino-4-oxo-2,3,4,5-tetrahydro-1,5-benzothiazepine-5-acetic acid as colorless prisms, m.p. 207°–210° C.

Elemental analysis, for $C_{21}H_{28}N_2O_5S\cdot H_2O$; Calcd.: C, 57.52; H, 6.89; N, 6.39; Found: C, 57.20; H, 6.91; N, 6.42.

$[\alpha]_D - 137°$ (c=1, in methanol).

EXAMPLE 51

A mixture of ethyl 3(R)-(1-ethoxycarbonyl-5-phthalimidopentyl)amino-4-oxo-2,3,4,5-tetrahydro-1,5-benzothiazepine-5-acetate (0.7 g) obtained in Reference Example 37, ethanol (20 ml) and 85% hydrazine hydrate (0.3 g) is allowed to stand at room temperature. After 1 hour and 2 hours, 0.3 g each of hydrazine hydrate is further added to the mixture. The mixture is left standing overnight, then it is concentrated under reduced pressure. To the concentrate is added water. The resulting aqueous solution is saturated with sodium chloride and extracted 3 times with ethyl acetate (100 ml each). The extract is washed successively with 0.1N aqueous sodium hydroxide (50 ml) and water (100 ml) and dried over anhydrous magnesium sulfate. Next, the solution is treated with hydrogen chloride-ethyl acetate solution (5N, 0.5 ml) and concentrated under reduced pressure. The residue is triturated with ethyl ether to give ethyl 3(R)-(5-amino-1-ethoxycarbonylpentyl)amino-4-oxo-2,3,4,5-tetrahydro-1,5-benzothiazepine-5-acetate dihydrochloride (0.13 g) as colorless powder.

Elemental analysis, for $C_{21}H_{31}N_3O_5S\cdot 2HCl\cdot H_2O$; Calcd.: C, 47.73; H, 6.67; N, 7.95; Found: C, 47.81; H, 6.53: N, 7.83.

Mass spectrum (m/e): 437 (M+).

EXAMPLE 52

(1) Ethyl 3(R)-(5-amino-1-ethoxycarbonylpentyl)-amino-4-oxo-2,3,4,5-tetrahydro-1,5-benzothiazepine-5-acetate dihydrochloride (50 mg) obtained in Example 51 is dissolved in a mixture of ethyl acetate (30 ml) and water (10 ml). To the mixture are added benzyloxycarbonyl chloride (0.15 ml) and sodium bicarbonate (0.3 g), and the resulting mixture is stirred for 2.5 hours at room temperature. Ethyl acetate layer is separated, washed with water, dried over anhydrous magnesium sulfate and concentrated under reduced pressure. The oily residue is dissolved in a mixture of ethyl ether (20 ml) and petroleum ether (20 ml) and treated with hydrogen chloride-ethyl acetate solution (5N, 0.2 ml) to precipitate ethyl 3(R)-(5-benzyloxycarbonylamino-1-ethoxycarbonylpentyl)amino-4-oxo-2,3,4,5-tetrahydro-1,5-benzothiazepine-5-acetate hydrochloride (55 mg) as colorless powder.

Mass spectrum (m/e): 571 (M+).

(2) Ethyl 3(R)-(5-benzyloxycarbonylamino-1-ethoxycarbonylpentyl)amino-4-oxo-2,3,4,5-tetrahydro-1,5-benzothiazepine-5-acetate hydrochloride (55 mg) obtained in Example 52-(1) is dissolved in a mixture of ethanol (3 ml) and 1N aqueous sodium hydroxide (2 ml). The solution is allowed to stand for 1 hour at room temperature, diluted with water (50 ml) and extracted with ethyl ether (20 ml). The aqueous layer is acidified to pH 4 with 1N hydrochloric acid, saturated with ammonium chloride and extracted ten times with ethyl acetate (20 ml each). The extract is washed with a small amount of water, dried over anhydrous magnesium sulfate and concentrated to dryness under reduced pressure to yield 3(R)-(5-benzyloxycarbonylamino-1-carboxypentyl)amino-4-oxo-2,3,4,5-tetrahydro-1,5-benzothiazepine-5-acetic acid (40 mg) as colorless powder.

Mass spectrum (m/e): 515 (M+).

(3) To a solution of 3(R)-(5-benzyloxycarbonylamino-1-carboxypentyl)amino-4-oxo-2,3,4,5-tetrahydro-1,5-benzothiazepine-5-acetic acid (40 mg) obtained in Example 52-(2) in acetic acid (1 ml) is added 30% hydrogen bromide-acetic acid solution (1 ml). The resulting mixture is allowed to stand for 1 hour at room temperature and diluted with a mixture ethyl ether (80 ml) and petroleum ether (20 ml), followed by stirring. The supernatant layer is removed by decantation, and precipitate is collected and dried to provide 3(R)-(5-amino-1-carboxypentyl)amino-4-oxo-2,3,4,5-tetrahydro-1,5-benzothiazepine-5-acetic acid dihydrobromide (33 mg) as colorless powder.

SIMS spectrum (m/e): 382 (MH+); addition of potassium iodide 420 (M+K)+.

EXAMPLE 53

Ethyl 3(R)-[2(S)-benzyloxycarbonylamino-1-ethoxycarbonyl-3-phenylpropyl]amino-4-oxo-2,3,4,5-tetrahydro-1,5-benzothiazepine-5-acetate (0.22 g) obtained in Reference Example 39 is treated with hydrogen bromide in a manner similar to that described in Example 52-(3) to yield ethyl 3(R)-[2(S)-amino-1-ethoxycarbonyl-3-phenylpropyl]-amino-4-oxo-2,3,4,5-tetrahydro-1,5-benzothiazepine-5-acetate dihydrobromide (0.18 g) as colorless powder.

Elemental analysis, for $C_{25}H_{31}N_3O_5S\cdot 2HBr\cdot H_2O$; Calcd.: C, 45.12; H, 5.30; N, 6.31; Found: C, 45.11; H, 5.28; N, 6.27.

Mass spectrum (m/e): 485 (M+).

EXAMPLE 54

A mixture of ethyl 3(R)-[2(S)-amino-1-ethoxycarbonyl-3-phenylpropyl]amino-4-oxo-2,3,4,5-tetrahydro-1,5-benzothiazepine-5-acetate dihydrobromide (0.15 g) obtained in Example 53, methanol (5 ml) and 1N aqueous sodium hydroxide is allowed to stand for 1 hour at room temperature. After evaporation of methanol, the residue is diluted with water (10 ml) and submitted to Amberlite XAD-2 column chromatography eluting with methanol-water (1:1). The eluate is concentrated under reduced pressure and lyophilized to give disodium 3(R)-[2(S)-amino-1-carboxylato-3-phenylpropyl]amino-4-oxo-2,3,4,5-tetrahydro-1,5-benzothiazepine-5-acetate (37 mg) as colorless powder.

Elemental analysis, for $C_{21}H_{21}N_3Na_2O_5S\cdot 3/2H_2O$; Calcd.: C, 50.40; H, 4.83; N, 8.40; Found: C, 50.42; H, 5.08; N, 8.53.

SIMS spectrum (m/e): 474(MH+), 452, 430; 506, 468, 430, (addition of potassium iodide).

EXAMPLE 55

Two point five g of the tert-butyl 3(R)-amino-4-oxo-2,3,4,5-tetrahydro-1,5-benzothiazepine-5-α-methylacetate obtained in Reference Example 41 is allowed to react with ethyl 4-cyclohexyl-2-oxobutyrate in a manner similar to that described in Example 2. The product is purified by chromatography on silica gel using hexane-ethyl acetate (4:1) as an eluant to yield tert-butyl 3(R)-[1(R)-ethoxycarbonyl-3-cyclohexylpropyl]amino-4-oxo-2,3,4,5-tetrahydro-1,5-benzothiazepine-5-α-methylacetate as an oil from the first fraction.

Mass spectrum (m/e): 518 (M+).

From the second fraction tert-butyl 3(R)-[1(S)-ethoxycarbonyl-3-cyclohexylpropyl]amino-4-oxo-2,3,4,5-tetrahydro-1,5-benzothiazepine-5-α-methylacetate (0.28 g) as a colorless oil is obtained.

IR $\nu_{max}^{neat}$ cm$^{-1}$: 1740, 1670 (C=O).

$[\alpha]_D^{23}$ −222° (c=0.4 in methanol).

Mass spectrum (m/e): 518(M+).

EXAMPLES 56 AND 57

The derivatives of tert-butyl 1,5-benzothiazepine-5-α-methylacetate obtained in Example 55 are treated with hydrogen chloride in a manner similar to that described in Example 5 to give the compounds as shown in Table 15.

TABLE 15

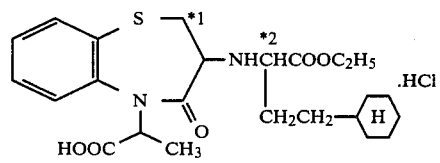

| Ex. No. | *1 | *2 | $[\alpha]_D$ (in methanol) |
|---------|----|----|------------------|
|         | Config. | | |
| 56      | R  | R  | −155° (c = 0.4) |

TABLE 15-continued

[Structure: benzothiazepine with S—*1, *2-NHCHCOOC₂H₅, CH₂CH₂—(cyclohexyl with H), HOOC-CH₃, N, O, .HCl]

Config.

| Ex. No. | *1 | *2 | $[\alpha]_D$ (in methanol) |
|---------|----|----|---------------------------|
| 57 | R | S | −132° (c = 0.4) |

EXAMPLES 58 AND 59

The derivatives of benzothiazepine obtained in Reference Examples 44 and 45 are treated with hydrogen chloride in a manner similar to that described in Example 5 to give the compounds as shown in Table 16 as colorless crystals.

TABLE 16

[Structure: benzothiazepine with S—*1, *2-NHCHCOOC₂H₅, CH₂CH₂CH₂CH₂NH₂, .2HCl, HOOC, N, O]

Config.

| Ex. No. | *1 | *2 | $[\alpha]_D$ (in methanol) |
|---------|----|----|---------------------------|
| 58 | R | R | −161° (c = 0.7) |
| 59 | R | S | −128° (c = 0.5) |

EXAMPLE 60

A mixture of 3(R)-[5-amino-1(S)-ethoxycarbonylpentyl]-amino-4-oxo-2,3,4,5-tetrahydro-1,5-benzothiazepine-5-acetic acid dihydrochloride (0.2 g) obtained in Example 59 and 1N aqueous sodium hydroxide (4 ml) is stirred at room temperature for 1.5 hours. After being acidified slightly with acetic acid (1 ml), the mixture is subjected to Amberlite XAD-2 column chromatography eluting with methanol-water (3:7). The eluate is concentrated under reduced pressure and lyophilized to give 3(R)-[5-amino-1(S)-carboxypentyl]amino-4-oxo-2,3,4,5-tetrahydro-1,5-benzothiazepine-5-acetic acid (0.1 g) as colorless powder.

Elemental analysis, for $C_{17}H_{23}N_3O_5S.H_2O$; Calcd.: C, 51.12; H, 6.31; N, 10.52; Found: C, 50.87; H, 5.83; N, 10.34.

$[\alpha]_D$−149° c=0.3 (in 1N hydrochloric acid).

SIMS spectrum (m/e): 382(MH+); addition of potassium iodide 420 (M+K)+.

EXAMPLE 61

Zero point three two g of tert-butyl 3(R)-[5-tert-butoxycarbonylamino-1(S)-carboxypentyl]amino-4-oxo-2,3,4,5-tetrahydro-1,5-benzothiazepine-5-acetic acid obtained in Reference Example 46 is treated with hydrogen chloride in a manner similar to that described in Example 5 to give 3(R)-[5-amino-1(S)-carboxypentyl]amino-4-oxo-2,3,4,5-tetrahydro-1,5-benzothiazepine-5-acetic acid dihydrochloride (0.26 g) as colorless crystals.

Elemental analysis, for $C_{17}H_{23}N_3O_5S.2HCl.CH_3COOC_2H_5$; Calcd.: C, 46.49; H, 6.13; N, 7.75; Found: C, 46.12; H, 6.16; N, 7.52.

This product is dissolved in 2 ml of water. After addition of 1N aqueous sodium hydroxide (0.5 ml) and acetic acid (0.5 ml), the solution subjected to Amberlite XAD-2 column chromatography in a manner similar to that described in Example 60 to yield the colorless powder (0.096 g) which is identical with the compound obtained in Example 60.

EXAMPLES 62–64

The derivatives of benzothiazepine obtained in Reference Examples 54–56 are treated with hydrogen chloride in a manner similar to that described in Example 5 to yield the compounds as shown in Table 17.

TABLE 17

[Structure: benzothiazepine with S—*1, —NH-*2-COOR¹², (CH₂)ₙNH₂, .2HCl, HOOC, N, O]

| Ex. No. | R¹² | n | Config. *1 | *2 | $[\alpha]_D$ (in methanol) |
|---------|-----|---|----|----|---------------------------|
| 62 | (CH₂)₃CH₃ | 4 | R | S | −123° (c = 0.4) |
| 63 | C₂H₅ | 2 | R | RS* | −144° (c = 0.4) |
| 64 | C₂H₅ | 6 | R | RS* | −118° (c = 0.4) |

*mixture of diastereomers

EXAMPLE 65

A half g of tert-butyl 3(R)-[1(S)-ethoxycarbonyl-5-phthalimidopentyl]amino-4-oxo-2,3,4,5-tetrahydro-1,5-benzothiazepine-5-acetate obtained in Reference Example 42 or 47 is treated with hydrazine in a manner similar to that described in Reference Example 44. The residue is allowed to react with benzoyl chloride to yield tert-butyl 3(R)-[5-benzoylamino-1(S)-ethoxycarbonylpentyl]-amino-4-oxo-2,3,4,5-tetrahydro-1,5-benzothiazepine-5-acetate (0.14 g) as a colorless oil.

IR $\nu_{max}^{neat}$ cm$^{-1}$: 3350(NH); 1740(ester); 1660(amido).

EXAMPLE 66

A half g of tert-butyl 3(R)-[1(S)-ethoxycarbonyl-5-phthalimidopentyl]amino-4-oxo-2,3,4,5-tetrahydro-1,5-benzothiazepine-5-acetate is treated with hydrazine in a manner similar to that described in Reference Example 44, and then reacted with acetyl chloride to give tert-butyl 3(R)-[5-acetylamino-1(S)-ethoxycarbonylpentyl]-amino-4-oxo-2,3,4,5-tetrahydro-1,5-benzothiazepine-5-acetate (0.25 g) as a colorless oil.

IR $\nu_{max}^{neat}$ cm$^{-1}$: 3320(NH), 1730(ester), 1660(amido).

EXAMPLES 67 AND 68

The derivatives of benzothiazepine obtained Examples 65 and 66 are treated with hydrogen chloride-ethyl acetate solution in a manner similar to that described in Example 5 to yield the compounds as shown in Table 18.

TABLE 18

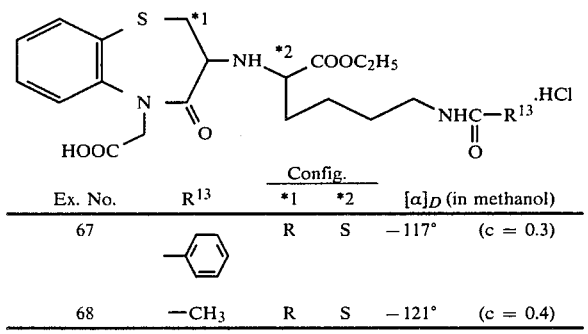

| Ex. No. | R[13] | Config. *1 *2 | [α]_D (in methanol) |
|---|---|---|---|
| 67 | —⟨phenyl⟩ | R  S | −117° (c = 0.3) |
| 68 | —CH₃ | R  S | −121° (c = 0.4) |

EXAMPLE 69

A mixture of 3(R)-[5-amino-1(S)-ethoxycarbonylpentyl]amino-4-oxo-2,3,4,5-tetrahydro-1,5-benzothiazepine-5-acetic acid dihydrochloride (0.2 g) obtained in Example 59, ethanol (10 ml), cyclohexanone (2 g) and sodium cyanoborohydride (0.3 g) is allowed to stand overnight at room temperature. To the residue, after evaporation of ethanol, is added 1N aqueous sodium hydroxide (4 ml). The resulting mixture is stirred at room temperature for 1 hour, diluted with water (20 ml) and extracted 3 times with ethyl acetate (20 ml each). The aqueous layer is slightly acidified with acetic acid (1 ml) and subjected to Amberlite XAD-2 column chromatography eluting with methanol-water (1:1). The eluate is concentrated under reduced pressure and lyophilized to give 3(R)-[1(S)-carboxy-5-cyclohexylaminopentyl]amino-4-oxo-2,3,4,5-tetrahydro-1,5-benzothiazepine-5-acetic acid (0.12 g) as colorless powder.

Elemental analysis, for $C_{23}H_{33}N_3O_5S \cdot H_2O$; Calcd.: C, 57.36; H, 7.32; N, 8.72; Found: C, 56.86; H, 7.48; N, 8.34.

$[\alpha]_D$ −117° (c=0.5 in methanol).

SIMS spectrum (m/e): 464(MH⁺); addition of potassium iodide 502(M+K)⁺, 464.

EXAMPLES 70 AND 71

3(R)-[5-Amino-1(S)-ethoxycarbonylpentyl]amino-4-oxo-2,3,4,5-tetrahydro-1,5-benzothiazepine-5-acetic acid dihydrochloride obtained in Example 59 is allowed to react with carbonyl compounds as shown in Table 19 and subsequently hydrolyzed in a manner similar to that described in Example 69 to give the compounds as shown in Table 19.

TABLE 19

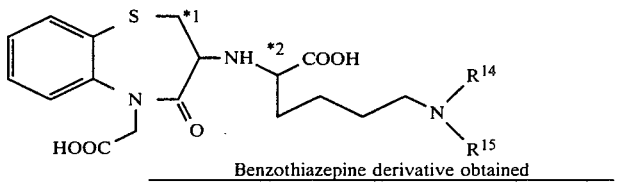

Benzothiazepine derivative obtained

| Ex. No. | Carbonyl compound used | Config. *1 *2 | N(R[14])(R[15]) | [α]_D (in methanol) | SIMS spectrum m/e(MH⁺) |
|---|---|---|---|---|---|
| 70 | CH₃(CH₂)₂CHO | R  S | N((CH₂)₃CH₃)((CH₂)₃CH₃) | −106° (c = 0.3) | 494 |
| 71 | (CH₃)₂CO | R  S | NHCH(CH₃)₂ | −129° (c = 0.2) | 424 |

EXAMPLE 72

To a stirred mixture of 3(R)-[7-amino-1-ethoxycarbonylheptyl]amino-4-oxo-2,3,4,5-tetrahydro-1,5-benzothiazepine-5-acetic acid dihydrochloride (0.7 g) obtained in Example 64, triethylamine (0.5 g) and ethyl acetate (10 ml) is added di-tert-butyl dicarbonate (0.45 g) at room temperature. After being stirred for 4 hours, the mixture is diluted with ethyl acetate (100 ml) and washed with water (5 ml). The ethyl acetate layer is dried over anhydrous magnesium sulfate and evaporated under reduced pressure to give a colorless oily residue, which is submitted to silica gel column chromatography using hexane-acetone-acetic acid (70:30:1) as an eluant.

The first fraction gives 3(R)-[7-tert-butoxycarbonylamino-1(S)-ethoxycarbonylheptyl]amino-4-oxo-2,3,4,5-tetrahydro-1,5-benzothiazepine-5-acetic acid as a colorless oil. From the second fraction, 3(R)-[7-tert-butoxycarbonylamino-1(R)-ethoxycarbonylheptyl]amino-4-oxo-2,3,4,5-tetrahydro-1,5-benzothiazepine-5-acetic acid is obtained as a colorless oil.

A solution of 3(R)-[7-tert-butoxycarbonylamino-1(S)-ethoxycarbonylheptyl]amino-4-oxo-2,3,4,5-tetrahydro-1,5-benzothiazepine-5-acetic acid obtained from the first fraction in hydrogen chloride-ethyl acetate solution (5N, 5 ml) is allowed to stand for 1 hour at room temperature. To the solution is added a mixture of ethyl ether and petroleum ether (2:1, 50 ml), and the resulting mixture is agitated thoroughly. The supernatant is removed by decantation and the precipitate is collected and dried under reduced pressure to yield 3(R)-[7-amino-1(S)-ethoxycarbonylheptyl]amino-4-oxo-2,3,4,5-tetrahydro-1,5-benzothiazepine-5-acetic acid dihydrochloride (0.2 g) as a colorless powder.

$[\alpha]_D$ −122° (C=0.2 in methanol).

A solution of 3(R)-[7-tert-butoxycarbonylamino-1(R)-ethoxycarbonylheptyl]amino-4-oxo-2,3,4,5-tetrahydro-1,5-benzothiazepine-5-acetic acid obtained from the second fraction in hydrogen chloride-ethyl acetate solution (5N, 5 ml) is allowed to stand for 1 hour at room temperature.

To the solution is added a mixture of ethyl ether and petroleum ether (2:1, 50 ml), and the resulting mixture is agitated thoroughly. The supernatant is removed by decantation and the precipitate is collected and dried under reduced pressure to give 3(R)-[7-amino-1(R)-ethoxycarbonylheptyl]amino-4-oxo-2,3,4,5-tetrahydro-1,5-benzothiazepine-5-acetic acid dihydrochloride (0.18 g) as a colorless powder.

$[\alpha]_D$ −136° (C=0.6 in methanol).

EXAMPLE 73

A solution of 3(R)-[7-amino-1(S)-ethoxycarbonylheptyl]amino-4oxo-2,3,4,5-tetrahydro-1,5-benzothiazepine-5-acetic acid dihydrochloride (0.16 g) obtained in Example 72 in 1N sodium hydroxide (4 ml) is allowed to stand for 30 minutes at room temperature. After addition of acetic acid (2 ml) and water (5 ml), the mixture is submitted to Amberlite XAD-2 column chromatography eluting with methanol-water (1:1). The eluate is concentrated under reduced pressure and lyophilized to yield 3(R)-[7-amino-1(S)-carboxyheptyl]amino-4-oxo-2,3,4,5-tetrahydro-1,5-benzothiazepine-5-acetic acid (0.11 g) as a colorless powder.

$[\alpha]_D$ −148° (C=0.6 in methanol).

EXAMPLE 74

A solution of tert-butyl 3(R)-[10-tert-butoxycarbonylamino-1(S)-ethoxycarbonyldecyl]amino-4-oxo-2,3,4,5-tetrahydro-1,5-benzothiazepine-5-acetate (0.3 g) in a hydrogen chloride-ethyl acetate solution (5N, 10 ml) stands for 3 hours at room temperature, and then a mixture of ether and petroleum ether is added. After agitating thoroughly, the supernatant is removed by decantation. The deposited precipitate is dried under reduced pressure to provide 3(R)-[10-amino-1(S)-ethoxycarbonyldecyl]amino-4-oxo-2,3,4,5-tetrahydro-1,5-benzothiazepine-5-acetic acid dihydrochloride (0.23) g as a colorless powder.

$[\alpha]_D$ −116° (c=0.1 in methanol).

EXAMPLE 75

A solution of 3(R)-[10-amino-1(S)-ethoxycarboxyldecyl]amino-4-oxo-2,3,4,5-tetrahydro-1,5-benzothiazepine-5-acetic acid (0.28 g) obtained in Example 74 in 1N sodium hydroxide (7 ml) stands for 1 hour at room temperature. After addition of acetic acid (2 ml) and water (5 ml), the mixture is subjected to Amberlite XAD-2 column chromatography (methanol:-water=1:1). The eluate is concentrated under reduced pressure. The deposited crystal is collected by filtration and dried to yield 3(R)-[10-amino-1(S)-carboxydecyl]amino-4-oxo-2,3,4,5-tetrahydro-1,5-benzothiazepine-5-acetic acid (0.12 g).

$[\alpha]_D$ −151° [c=0.1 in methanol-water (1:1)].

EXPERIMENT EXAMPLE 1

Experiment on Inhibition of Angiotensin I Converting Enzyme (ACE) by the Compounds of this Invention.

EXPERIMENTAL METHOD

The experiment was conducted in accordance with a modification of the method described by Cushman et al. (Biochemical Pharmacology, Vol. 20, pp. 1637, 1971). That is, using hippuryl-L-histidyl-L-leucine (HHL) as the substrate, the ACE inhibitory activity was determined in terms of percent inhibition on the amount of hippuric acid produced by ACE when the compound of the present invention was added. A solution of the compound of the present invention dissolved in 0.02 to 0.5% dimethylsulfoxide-100 mM borate-HCl buffer solution (pH 8.3, containing 300 mM sodium chloride) was added to 100 μl of ACE (protein concentration, 20 mg/ml) and 100 μl of 1.25 mM HHL. In this experiment, a borate-HCl buffer solution containing dimethylsulfoxide at a concentration equal to that of the test solution was used as a control. After warming the solution at 37° C. for 1 hour, 150 μl of 1N hydrochloric acid was added to the solution to terminate the reaction. After 0.8 ml of ethyl acetate was added the solution was centrifuged at 11500 rpm for 2 minutes. A 0.5 ml aliquot was separated from the ethyl acetate layer and dried at a temperature below 40° C. under nitrogen gas streams. The residue was mixed thoroughly with 4.5 ml of distilled water, and the mixture was subjected to colorimetry at a wavelength of 228 nm.

TEST RESULTS

The test results obtained with regard to the compounds of the present invention are as shown in Table 20.

TABLE 20

| Ex. No. of tested compound | Concentration (μM) | ACE inhibitory activity (%) |
|---|---|---|
| 5 | 0.1 | 40 |
|   | 1 | 84 |
| 6 | 0.1 | 48 |
|   | 1 | 85 |
| 7 | 0.1 | 53 |
|   | 1 | 86 |
| 9 | 0.1 | 83 |
|   | 1 | 95 |
| 12 | 1 | 50 |
|   | 10 | 86 |
| 13 | 0.01 | 46 |
|   | 0.1 | 91 |
| 50 | 0.01 | 77 |
|   | 0.1 | 96 |
| 60 | 0.1 | 82 |
|   | 1 | 98 |
| 69 | 0.1 | 93 |
|   | 1 | 100 |
| 73 | 0.1 | 96 |
|   | 1 | 100 |

EXPERIMENT EXAMPLE 2

Effect of the Compounds of the Present Invention against Hypertensive Activity of Angiotensin I.

EXPERIMENTAL METHOD

Male rats (Sprague-Dawley) weighing 250 to 350 g which were fed under free access to drinking water and feed were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II. And the tubes were fixed.

On the test day, an average blood pressure in the control phase was measured by an electric hemodynamometer (MPU-0.5-290-0-III model manufactured by NEC-Sanei, Japan) and recorded by a polygraph (NEC-Sanei, Type 365 or Nippon Kohden Type RM-45), and thereafter angiotensin I and then angiotensin II were injected through the femoral vein at a dose of 300 ng/kg and 100 ng/kg, respectively, to measure the hypertensive activity. Then, 3 and 10 mg/kg of the compound of the present invention were administered orally as an aqueous solution or an aqueous gum arabic suspension, and 20, 60 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

tensive activity of angiotensin I, the percent inhibitory value was corrected based on the variation with time in the hypertensive reaction by antiotensin II.

TEST RESULTS

The test results obtained with regard to the compounds of the present invention are as shown in Table 22.

TABLE 22

[Structure: benzothiazepine with S, N-CH(CH$_2$CH$_2$CH$_2$CH$_2$CH$_2$CH$_2$NH$_2$)-COOR (*2), N-CH$_2$COOH, and (*1) on S-bearing carbon]

| R (salt) | Config. *1 | Config. *2 | Dose μg/kg (i.v.) | After 5 min | After 10 min | After 30 min | After 60 min | After 90 min | After 120 min |
|---|---|---|---|---|---|---|---|---|---|
| | | | | \multicolumn{6}{c}{Inhibition against hypertensive reaction by angiotensin I (%)} |
| H | R | S | 300 | 100 | 97 | 97 | 91 | 78 | 48 |
| C$_2$H$_5$ (dihydrochloride) | R | S | 300 | 97 | 97 | 100 | 96 | 87 | 73 |

TEST RESULTS

The test results obtained with regard to the compounds of the present invention are as shown in Table 21.

TABLE 21

| Ex. No. of tested compound | Dose mg/kg (orally) | Inhibition against hypertensive reaction by angiotensin I (%) | | |
|---|---|---|---|---|
| | | After 20 min. | After 60 min. | After 120 min. |
| 7 | 3 | 85 | 51 | 27 |
|   | 10 | 85 | 68 | 51 |
| 9 | 3 | 66 | 36 | 12 |
|   | 10 | 92 | 72 | 68 |

EXPERIMENT EXAMPLE 3

Effect of the Compounds of the Present Invention against Hypertensive Activity of Angiotensin I.

EXPERIMENTAL METHOD

Male rats (Sprague-Dawley) weighing 300 to 400 g which were fed under free access to drinking water and feed were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II. And the tubes were fixed.

On the test day, an average blood pressure in the control phase was measured by an electric hemodynamometer (MPU-0.5-290-0-III model manufactured by NEC-Sanei, Japan) and recorded by a polygraph (NEC-Sanei, Type 365 or Nippon Kohden Type RM-45, and thereafter angiotensin I and then angiotensin II were injected through the femoral vein at a dose of 300 ng/kg and 100 ng/kg, respectively, to measure the hypertensive activity. Then, 300 ng/kg of the compound of the present invention were administered intravenously as a saline solution, and 5, 10, 30, 60, 90 and 120 minutes after the administration, angiotensin I and II were injected repeatedly to trace hypertensive reactions. In calculating the percent inhibition to the hyper-

PREPARATION EXAMPLE

The compounds (I) of the present invention can be used, for example, in the following examples of formulation.

1. (i) Tablets

| | |
|---|---|
| (1) 3(R)-[1(S)-Ethoxycarbonyl-3-phenylpropyl]amino-4-oxo-2,3,4,5-tetrahydro-1,5-benzothiazepine-5-acetic acid hydrochloride | 10 g |
| (2) Lactose | 90 g |
| (3) Corn starch | 29 g |
| (4) Magnesium stearate | 1 g |
| | 130 g for 1000 tablets |

The above ingredients (1) and (2) and 17 g of (3) are blended, and granulated together with a paste prepared from 7 g of the ingredient (3). Five g of the ingredient (3) and the ingredient (4) are added to the resulting granules, and the mixture is compressed by a tabletting machine to prepare 1000 tablets of a diameter of 7 mm each containing 10 mg of the ingredient (1).

(ii) Tablets

3(R)-[1(S)-Carboxy-5-cyclohexylaminopentyl]amino-4-oxo-2,3,4,5-tetrahydro-1,5-benzothiazepine-5-acetic acid (10 g) is used as the ingredient (1) and treated in a manner similar to that of Preparation Eample 1(i) to prepare tablets.

2. Capsules

| | |
|---|---|
| (1) 3 (R)-[1(S)-Ethoxycarbonyl-3-cyclohexylpropyl]amino-4-oxo-2,3,4,5-tetrahydro-1,5-bezothiazepine-5-acetic acid hydrochloride | 10 g |
| (2) Lactose | 135 g |
| (3) Finely powdered cellulose | 70 g |
| (4) Magnesium stearate | 5 g |
| | 220 g for 1000 capsules |

All of the above ingredients are blended and filled into 1000 capsules of Gelatin Capsule No. 3 (X Japanese Pharmacopoiea) to prepare 1000 capsules each containing 10 mg of the ingredient (1).

3. (i) Injectable solution

| (1) Monosodium 3(R)-[1(S)-carboxy-3-phenyl-propyl]amino-4-oxo-2,3,4,5-tetrahydro-1,5-benzothiazepine-5-acetate | 10 g |
|---|---|
| (2) Sodium chloride | 9 g |
| (3) Chlorobutanol | 5 g |

All of the above ingredients are dissolved in 1000 ml of distilled water and charged into 1000 brown ampoules each containing 1 ml of the solution. The air in the ampoules is replaced with nitrogen gas and the ampoules are sealed. The entire preparation steps are conducted under sterile conditions.

(ii) Injectable solution

| (1) 3(R)-[5-Amino-1(S)-carboxypentyl]amino-4-oxo-2,3,4,5-tetrahydro-1,5-benzothiazepine-5-acetic acid | 10 g |
|---|---|
| (2) Sodium chloride | 9 g |

The ingredients (1) and (2) are dissolved in 1000 ml of distilled water and charged into 1000 brown ampoules each containing 1 ml of the solution. The air of the ampoules is replaced with nitrogen gas and the ampoules are sealed. The entire preparation steps are conducted under sterile conditions.

INDUSTRIAL APPLICABILITY

The condensed, seven-membered ring compounds (I) as provided by the present invention each have excellent pharmacological action, and are useful as pharmaceuticals.

What is claimed is:

1. A compound of the formula

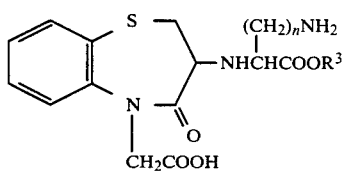

wherein $R^3$ is hydrogen or $C_{1-4}$ alkyl and n is 6 or 7, or a pharmaceutically acceptable salt thereof.

2. A compound according to claim 1, wherein n is 6.

3. The compound according to claim 1 which is 3(R)-[7-amino-1-(S)-carboxyheptyl]-amino-4-oxo-2,3,4,5-tetrahydro-1,5-benzothiazepine-5-acetic acid.

4. The compound according to claim 1 which is 3(R)-[7-amino-1-(S)-ethoxycarbonylheptyl]amino-4-oxo-2,3,4,5-tetrahydro-1,5-benzothiazepine-5-acetic acid.

5. The compound according to claim 1 which is 3(R)-[7-amino-1-(S)-ethoxycarbonylheptyl]amino-4-oxo-2,3,4,5-tetrahydro-1,5-benzothiazepine-5-acetic acid dihydrochloride.

6. A compound according to claim 1 which is 3(R)-[8-amino-1(S)-carboxyoctyl]amino-4-oxo-2,3,4,5-tetrahydro-1,5-benzothiazepine-5-acetic acid.

7. A compound according to claim 1 which is 3(R)-[8-amino-1(S)-ethoxycarbonyloctyl]amino-4-oxo-2,3,4,5-tetrahydro-1,5-benzothiazepine-5-acetic acid.

8. A pharmaceutical composition suitable for treatment of hypertension which comprises, as an active ingredient, an effective anti-hypertensive amount of a compound of the formula

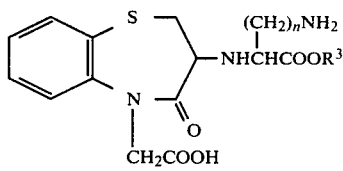

wherein $R^{3'}$ is hydrogen or $C_{1-4}$ alkyl and n is 6 or 7 or a pharmaceutically acceptable salt thereof, and a pharmaceutically acceptable carrier, excipient or diluent therefor.

9. A method for treatment of hypertension in a mammal, which comprises administering to said mammal an effective antihypertensive amount of a compound of the formula

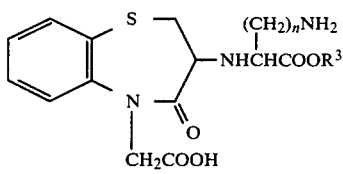

wherein $R^{3'}$ is hydrogen or $C_{1-4}$ alkyl a nd n is 6 or 7 or a pharmaceutically acceptable salt thereof.

* * * * *